United States Patent
Ikeda et al.

(10) Patent No.: US 12,030,002 B2
(45) Date of Patent: Jul. 9, 2024

(54) FILTRATION RECOVERY DEVICE AND FILTRATION RECOVERY METHOD

(71) Applicant: Murata Manufacturing Co., Ltd., Nagaokakyo (JP)

(72) Inventors: Miki Ikeda, Nagaokakyo (JP); Miwako Nishikawa, Nagaokakyo (JP); Toshikazu Kawaguchi, Nagaokakyo (JP); Takashi Kondo, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 873 days.

(21) Appl. No.: 17/095,419

(22) Filed: Nov. 11, 2020

(65) Prior Publication Data

US 2021/0060457 A1    Mar. 4, 2021

Related U.S. Application Data

(63) Continuation of application No. PCT/JP2019/026251, filed on Jul. 2, 2019.

(30) Foreign Application Priority Data

Jul. 3, 2018  (JP) .................. 2018-126593

(51) Int. Cl.
*B01D 29/05*   (2006.01)
*B01D 29/78*   (2006.01)
(Continued)

(52) U.S. Cl.
CPC ............. *B01D 29/05* (2013.01); *B01D 29/78* (2013.01); *B01D 39/2027* (2013.01);
(Continued)

(58) Field of Classification Search
CPC .... B01D 29/05; B01D 29/78; B01D 39/2027; B01D 39/2068; B01D 2201/0415; C12M 1/12; C12M 1/28
(Continued)

(56) References Cited

U.S. PATENT DOCUMENTS 4,683,058 A    7/1987  Lyman et al.
5,308,483 A *  5/1994  Sklar .................... B01D 63/087
                                                    73/863.25
(Continued)

FOREIGN PATENT DOCUMENTS

CN    108025238 A    5/2018
JP    S62221459 A    9/1987
(Continued)

OTHER PUBLICATIONS

Machine-generated English translation of WO 2017/159367, generated on Oct. 13, 2023.*
(Continued)

*Primary Examiner* — Fred Prince
(74) *Attorney, Agent, or Firm* — ArentFox Schiff LLP

(57) ABSTRACT

A filtration recovery device according to the present disclosure may include: a filtration filter having a plurality of through-holes; and a holder having an introduction port configured to introduce a liquid, a discharge port configured to discharge the liquid, and a flow path configured to communicate the introduction port and the discharge port with each other, in which the filtration filter is disposed in the flow path between the introduction port and the discharge port of the holder.

17 Claims, 15 Drawing Sheets

(51) Int. Cl.
  *B01D 39/20* (2006.01)
  *C12M 1/12* (2006.01)
  *C12M 1/28* (2006.01)

(52) U.S. Cl.
  CPC .......... *B01D 39/2068* (2013.01); *C12M 1/12* (2013.01); *C12M 1/28* (2013.01); *B01D 2201/0415* (2013.01)

(58) Field of Classification Search
  USPC .............. 210/470, 473, 474, 477, 232, 348
  See application file for complete search history.

(56) References Cited

U.S. PATENT DOCUMENTS

| | | | | |
|---|---|---|---|---|
| 6,280,621 | B1* | 8/2001 | Yazawa | B01D 61/20 422/534 |
| 2006/0144781 | A1* | 7/2006 | Carlson | B01D 61/20 210/473 |
| 2011/0178424 | A1* | 7/2011 | Wilkinson | A61B 10/0096 600/573 |
| 2011/0233148 | A1* | 9/2011 | Antonchuk | B01D 35/30 210/477 |
| 2011/0300609 | A1 | 12/2011 | Lim et al. | |
| 2017/0282180 | A1 | 10/2017 | Yagi et al. | |
| 2018/0243672 | A1 | 8/2018 | Banju et al. | |
| 2018/0362917 | A1 | 12/2018 | Kondo et al. | |

FOREIGN PATENT DOCUMENTS

| | | |
|---|---|---|
| JP | 2004317179 A | 11/2004 |
| JP | 2011525805 A | 9/2011 |
| JP | 2013141456 A | 7/2013 |
| WO | 2016031971 A1 | 3/2016 |
| WO | 2017159367 A1 | 9/2017 |
| WO | WO 2017/159367 A1 * | 9/2017 |
| WO | 2018003104 A1 | 1/2018 |

OTHER PUBLICATIONS

International Search Report Issued for PCT/JP2019/026251, dated Sep. 17, 2019.
Written Opinion of the International Searching Authority issued for PCT/JP2019/026251, dated Sep. 17, 2019.

* cited by examiner

FILTRATION RECOVERY DEVICE AND FILTRATION RECOVERY METHOD

CROSS REFERENCE TO RELATED APPLICATIONS

This application is a continuation of International Application No. PCT/JP2019/026251, filed Jul. 2, 2019, which claims priority to Japanese Patent Application No. 2018-126593, filed Jul. 3, 2018, the entire contents of each of which are hereby incorporated in their entirety.

TECHNICAL FIELD

Aspects of the present disclosure are directed to a filtration recovery device and a filtration recovery method.

BACKGROUND OF THE INVENTION

Japanese Unexamined Patent Application Publication No. 2013-1414561 discloses a device for filtering a liquid containing a filtration object, for example, a cell strainer. The cell strainer has a filtering portion, a filter, that is opened upward and filters a liquid, a holding portion that holds the filtering portion in an opening portion, and a communication portion that, when being held by a tube, communicates the inside and the outside of the tube. In the cell strainer, the filtering portion is disposed on a side surface and a bottom surface of the holding portion. However, the cell strainer still leaves room for improvement in terms of achieving easy recovery of the filtration object.

SUMMARY OF THE INVENTION

Accordingly, it is an object of the present invention of the present invention to provide a filtration recovery device and a filtration recovery method capable of easily recovering a filtration object.

A filtration recovery device according to one aspect of the present disclosure may include: a filtration filter having a plurality of through-holes; and a holder having an introduction port configured to introduce a liquid, a discharge port configured to discharge the liquid, and a flow path configured to communicate the introduction port and the discharge port with each other, in which the filtration filter is disposed in the flow path between the introduction port and the discharge port of the holder.

A filtration recovery method according to one aspect of the disclosure is a filtration recovery method for filtering a liquid containing a filtration object and recovering the filtration object, the filtration recovery method includes the steps of: capturing, by using a filtration recovery device that includes a filtration filter having a plurality of through-holes, and a holder having an introduction port configured to introduce a liquid, a discharge port configured to discharge the liquid, and a flow path configured to communicate the introduction port and the discharge port with each other, and in which the filtration filter is disposed in the flow path between the introduction port and the discharge port of the holder, by filtering the liquid containing the filtration object, the filtration object by the filtration filter; closing the discharge port of the holder of the filtration recovery device; introducing a liquid for recovery from the introduction port of the holder of the filtration recovery device; and recovering the filtration object with the liquid for recovery held in the holder of the filtration recovery device.

According to the present disclosure, it is possible to provide a filtration recovery device and a filtration recovery method capable of easily recovering a filtration object.

Additional advantages and novel features of the system of the present disclosure will be set forth in part in the description that follows, and in part will become more apparent to those skilled in the art upon examination of the following or upon learning by practice of the disclosure.

BRIEF DESCRIPTION OF THE DRAWINGS

In the descriptions that follow, like parts are marked throughout the specification and drawings with the same numerals, respectively. The drawings are not necessarily drawn to scale and certain drawings may be shown in exaggerated or generalized form in the interest of clarity and conciseness. The disclosure itself, however, as well as a preferred mode of use, further features and advances thereof, will be understood by reference to the following detailed description of illustrative implementations of the disclosure when read in conjunction with reference to the accompanying drawings, wherein.

DETAILED DESCRIPTION

Figure 1:
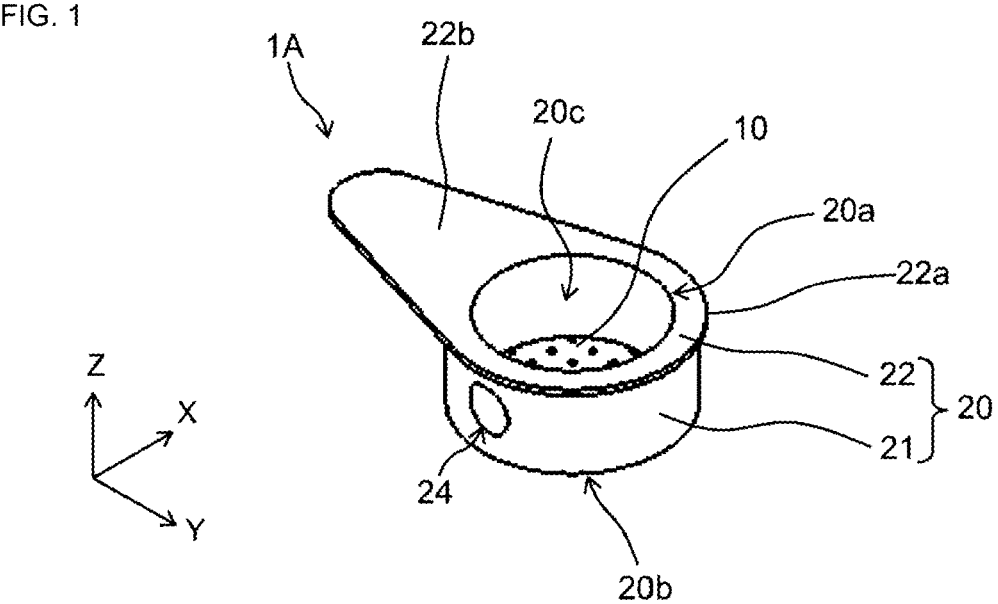
FIG. 1 is a schematic perspective view of an example of a filtration recovery device in accordance with aspects of the present disclosure.

When a liquid containing a filtration object is filtered using a filter, the filtration object is captured by the filter in a state of being exposed in the air. The filtration object that has been captured by the filter is recovered by a recovery instrument or the like, or recovered by turning over the filter.

In the recovery methods as described above, it is difficult to separate the filtration object from the filter, and it is not possible to easily recover the filtration object. This causes a problem such as that a recovery rate cannot be improved. In addition, in the case where the filtration object is a cell, there is a risk that the cell will be damaged due to physical contact of the recovery instrument or the like.

Aspects of the present disclosure have been researched, for example, after filtering a liquid containing a filtration object through a filter, bringing the filtration object which has been captured by the filter into a state of being immersed in a liquid for recovery, and recovering the filtration object with the liquid for recovery.

As a result, it has been discovered, in a device including a filtration filter and a holder for holding the filtration filter, by bringing the holder into a state in which a discharge port thereof is closed after the filtration is performed, holding the liquid for recovery inside the device. With this, when recovering the filtration object, by immersing the filtration object which has been captured by the filter in the liquid for recovery, releasing the filtration object from the filtration filter, and recovering the filtration object by the recovering instrument such as a pipette or the like.

Furthermore, it has been discovered, in the case where the filtration object is a cell, by using a solvent or the like as the liquid for recovery, by recovering the solvent together with the cell captured by the filter, generating a cell suspension. In addition, by adjusting the amount of the liquid for recovery to be introduced into the inside of the device, adjusting the liquid amount of the cell suspension to be generated.

Based on the above-described discoveries, a filtration recovery device according to one aspect of the disclosure may include: a filtration filter having a plurality of through-holes; and a holder having an introduction port configured to introduce a liquid, a discharge port configured to discharge the liquid, and a flow path configured to communicate the introduction port and the discharge port with each other, in which the filtration filter is disposed in the flow path between the introduction port and the discharge port of the holder. This configuration may make it possible to easily recover a filtration object.

In the filtration recovery device, a projection portion that is provided so as to project toward an inner side portion of the holder may be formed on an inner wall of the holder, and the projection portion may hold the filtration filter. This configuration may make it possible to hold the filtration filter above the discharge port by the projection portion, and may make it possible to easily recover the filtration object.

In the filtration recovery device, the projection portion may be formed at one end of the holder at which the discharge port is provided, and the filtration filter may be disposed at a position closer to the discharge port than the introduction port. This configuration may make it possible to reduce a liquid amount of a liquid for recovery introduced when recovering the filtration object.

In the filtration recovery device, the holder may have a first holder having a tubular shape and having the projection portion, and a second holder having a tubular shape and fitted into the first holder, and the filtration filter may be held between the projection portion of the first holder and one end of the second holder. This configuration may make it easier to hold the liquid for recovery inside the holder and may make it possible to easily recover the filtration object.

In the filtration recovery device, the first holder may include a first main body portion having a tubular shape and having a first end portion located on a side of the introduction port of the holder and a second end portion located on a side of the discharge port of the holder, the second holder may include a second main body portion having a tubular shape and having a third end portion located on the side of the introduction port of the holder and a fourth end portion located on the side of the discharge port of the holder, and an inner wall of the first holder and an outer wall of the second holder may be in surface contact with each other, the filtration filter may include a filter portion having the plurality of through-holes, and a frame portion disposed so as to surround an outer periphery of the filter portion, the projection portion may be provided at the second end portion of the first main body portion, an inner wall of the first main body portion and an outer wall of the second main body portion may be in surface contact with each other, and the frame portion of the filtration filter may be held between the fourth end portion of the second main body portion and an upper surface of the projection portion. This configuration may make it possible to suppress leakage of the liquid for recovery held inside the holder to the outside of the holder and may make it possible to easily recover the filtration object.

In the filtration recovery device, the second holder may have a flange extending from the outer wall of the second main body portion toward an outer side portion of the second holder at the third end portion of the second main body portion, and the flange may be in contact with the first end portion of the first main body portion. This configuration may make it easy to detach the second holder from the first holder.

In the filtration recovery device, the frame portion of the filtration filter may be held, in a thickness direction, between the projection portion of the first holder and the one end of the second holder, in a state of continuously extending in a direction from the filter portion toward the frame portion. This configuration may make it possible to hold the filtration filter in the flow path of the holder in a state where pulling force toward an outer side portion in the radial direction of the filtration filter is suppressed. As a result, breakage of the filtration filter during the filtration may be suppressed.

In the filtration recovery device, in or on the inner wall of the holder, a liquid amount indication portion configured to indicate a liquid amount of a liquid held inside the holder in a state where the discharge port is closed may be provided. This configuration may make it possible to adjust the liquid amount to be recovered when recovering the filtration object with the liquid for recovery.

In the filtration recovery device, the one end of the holder at which the discharge port is provided may be configured so as to make surface contact with a flat surface. This configuration may make it possible to suppress leakage of the liquid for recovery from the discharge port when the filtration recovery device is placed on the flat surface, and may make it possible to easily recover the filtration object.

In the filtration recovery device, the filtration filter may include a filter portion having at least one of a metal and a metal oxide as a main component and having the plurality of through-holes, and a frame portion disposed so as to surround an outer periphery of the filter portion. This configuration may make it possible to more easily recover the filtration object.

The filtration recovery device may further includes: a petri dish having a bottom surface portion and a side wall portion formed along an outer edge of the bottom surface portion and extending upward from the bottom surface portion, and attachable and detachable to the one end of the holder at which the discharge port is provided, in which the bottom surface portion of the petri dish may be disposed at the one end of the holder at which the discharge port is provided, and the side wall portion of the petri dish may surround an outer wall of the holder. This configuration may make it possible to suppress leakage of the liquid for recovery held in the holder, and therefore may make it possible to easily recover the filtration object.

A filtration recovery method according to one aspect of the disclosure is a filtration recovery method for filtering a liquid containing a filtration object and recovering the filtration object, the filtration recovery method includes the steps of: capturing, by using a filtration recovery device that includes a filtration filter having a plurality of through-holes, and a holder having an introduction port configured to introduce a liquid, a discharge port configured to discharge the liquid, and a flow path configured to communicate the introduction port and the discharge port with each other, and in which the filtration filter is disposed in the flow path between the introduction port and the discharge port of the holder, by filtering the liquid containing the filtration object, the filtration object by the filtration filter; closing the discharge port of the holder of the filtration recovery device; introducing a liquid for recovery from the introduction port of the holder of the filtration recovery device; and recovering the filtration object with the liquid for recovery held in the holder of the filtration recovery device. This configuration may make it possible to easily recover the filtration object.

In the filtration recovery method, the step of closing the discharge port of the holder of the filtration recovery device may include disposing one end of the holder at which the discharge port is provided on a bottom surface portion of a petri dish. This configuration may make it possible to more easily recover the filtration object.

In the filtration recovery method, in or on an inner wall of the holder of the filtration recovery device, a liquid amount indication portion configured to indicate a liquid amount of a liquid held inside the holder in a state where the discharge port is closed may be provided, and the step of introducing the liquid for recovery may include introducing the liquid for recovery based on the liquid amount indication portion. This configuration may make it possible to adjust the liquid amount of the liquid recovered with the filtration object.

A filtration recovery method according to one aspect of the disclosure is a filtration recovery method for filtering a liquid containing a filtration object and recovering the filtration object, the filtration recovery method may include the steps of: capturing, by using a filtration recovery device that includes a filtration filter having a plurality of through-holes, and a holder having an introduction port configured to introduce a liquid, a discharge port configured to discharge the liquid, and a flow path configured to communicate the introduction port and the discharge port with each other, and in which the filtration filter is disposed in the flow path between the introduction port and the discharge port of the holder, by filtering the liquid containing the filtration object, the filtration object by the filtration filter; detaching the filtration filter from the holder of the filtration recovery device; separating the filtration object captured by the filtration filter by a liquid for recovery; and recovering the filtration object with the liquid for recovery. This configuration may make it possible to easily recover the filtration object.

A filtration recovery method according to one aspect of the disclosure is a filtration recovery method for separating a cell from a cell aggregate and filtering out and recovering the cell, the filtration recovery method may include the steps of: introducing a cell aggregate into a filtration recovery device that includes a filtration filter having a plurality of through-holes, and a holder having an introduction port configured to introduce a liquid, a discharge port configured to discharge the liquid, and a flow path configured to communicate the introduction port and the discharge port with each other, and in which the filtration filter is disposed in the flow path between the introduction port and the discharge port of the holder; introducing a separation solution into the filtration recovery device; separating a cell from the cell aggregate by maintaining a state where the cell aggregate is immersed in the separation solution; capturing the cell by the filtration filter by discharging the separation solution from the filtration recovery device; and closing the discharge port of the holder of the filtration recovery device; introducing a liquid for recovery from the introduction port of the holder of the filtration recovery device; and recovering the cell with the liquid for recovery held in the holder of the filtration recovery device. This configuration may make it possible to easily recover the filtration object.

A filtration recovery method according to one aspect of the disclosure is a filtration recovery method for filtering a liquid containing a filtration object and recovering the filtration object, the filtration recovery method may include the steps of: introducing a solvent into a filtration recovery device that includes a filtration filter having a plurality of through-holes, and a holder having an introduction port configured to introduce a liquid, a discharge port configured to discharge the liquid, and a flow path configured to communicate the introduction port and the discharge port with each other, and in which the filtration filter is disposed in the flow path between the introduction port and the discharge port of the holder; capturing, by introducing the liquid containing the filtration object into the filtration recovery device, the filtration object by the filtration filter; closing the discharge port of the holder of the filtration recovery device; introducing a liquid for recovery from the introduction port of the holder of the filtration recovery device; and recovering the filtration object with the liquid for recovery held in the holder of the filtration recovery device. This configuration may make it possible to easily recover the filtration object.

Hereinafter, aspects of the present disclosure will be described with reference to the accompanying drawings. In addition, in the drawings, elements are exaggeratedly illustrated in order to facilitate understanding of the description.

A filtration recovery device according to an aspect of the present disclosure is a device capable of performing filtration and recovery. Specifically, the filtration recovery device filters a liquid containing a filtration object through a filtration filter and then holds a liquid for recovery inside the filtration recovery device. Thereafter, the filtration object captured by the filtration filter is recovered together with the liquid for recovery by a pipette or the like.

In the present specification, the "filtration object" means an object to be filtered out among objects contained in a liquid. For example, the filtration object may be a biologically derived substance contained in a liquid. The "biologically derived substance" means a substance derived from a living organism, such as a cell (eukaryote), bacteria (eubacteria), virus, and the like. Examples of the cell (eukaryote) include an induced pluripotent stem cell (iPS cell), an ES cell, a stem cell, a mesenchymal stem cell, a mononuclear cell, a single cell, a cell mass, a floating cell, an adherent cell, a nerve cell, a leukocyte, a cell for regenerative medicine, an autologous cell, a cancer cell, a circulating tumor cell (CTC) in blood, HL-60, HELA, and fungi. Examples of the bacteria (eubacteria) include *Escherichia coli* and *Mycobacterium tuberculosis*.

In an aspect of the present disclosure, as an example, the description will be given assuming that a liquid is a cell suspension, and the filtration object is a cell.

Figure 2:
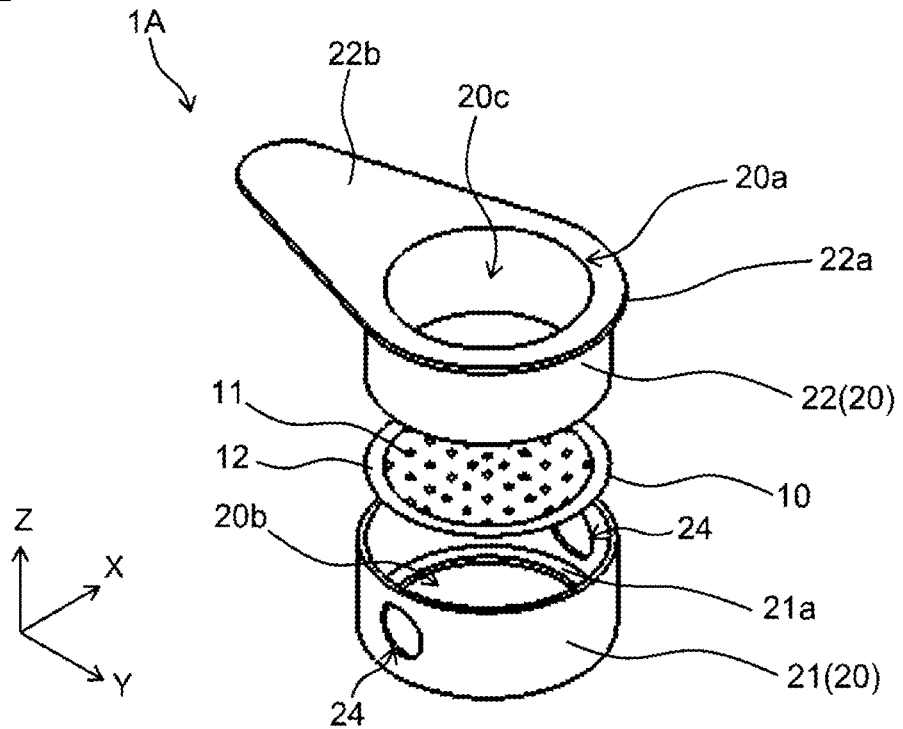
FIG. 2 is a schematic exploded perspective view of an example of the filtration recovery device in accordance with aspects of the present disclosure.
Figure 3:
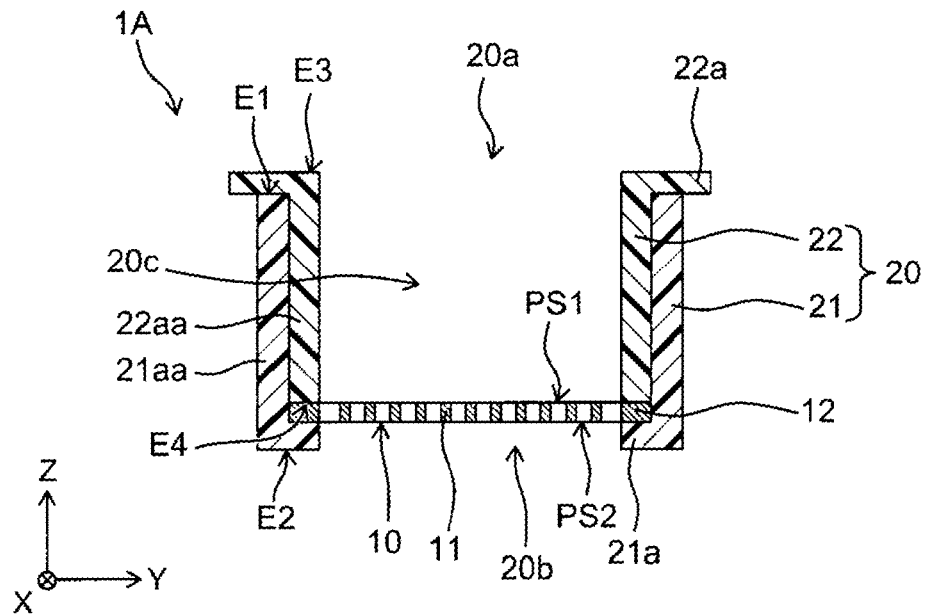
FIG. 3 is a schematic cross-sectional view of an example of the filtration recovery device in accordance with aspects of the present disclosure.

FIG. 1 is a schematic perspective view of an example of a filtration recovery device 1A according to an aspect of the present disclosure. FIG. 2 is a schematic exploded perspective view of the example of the filtration recovery device 1A according to an aspect of the present disclosure. FIG. 3 is a schematic cross-sectional view of the example of the filtration recovery device 1A according to an aspect of the present disclosure. In the drawings, X, Y, and Z directions represent the lateral direction, the longitudinal direction, and the thickness direction of the filtration recovery device 1A, respectively.

As illustrated in FIG. 1 to FIG. 3, the filtration recovery device 1A includes a filtration filter 10 and a holder 20 that holds the filtration filter 10.<Filtration Filter>

The filtration filter 10 is a metal filter. Specifically, the filtration filter 10 contains at least one of a metal and a metal oxide as a main component. The filtration filter 10 includes a filter portion 11 having a plurality of through-holes, and a frame portion 12 disposed so as to surround an outer periphery of the filter portion 11 according to an aspect of the present disclosure, the filter portion 11 and the frame portion 12 are formed integrally with each other.

Figure 4:
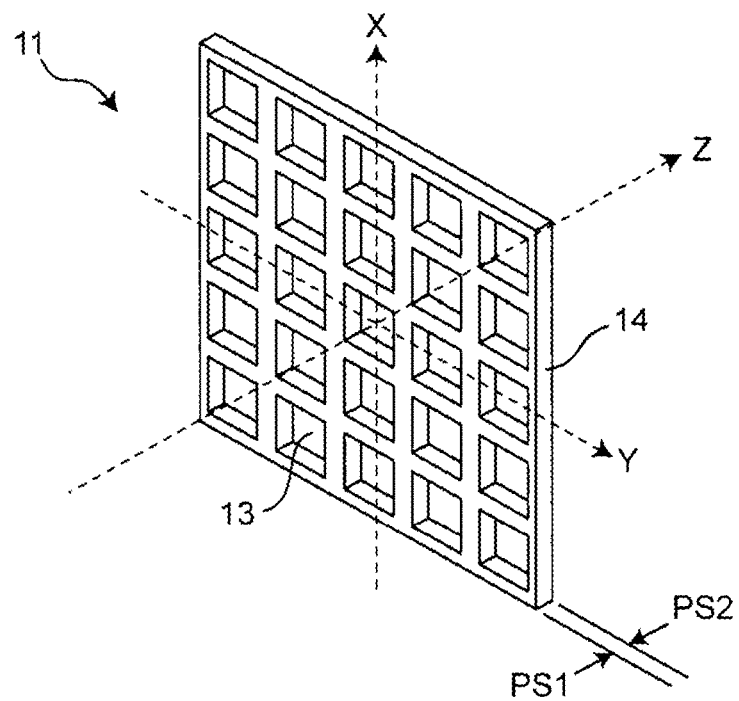
FIG. 4 is an enlarged perspective view of part of an exemplary filter portion.
Figure 5:
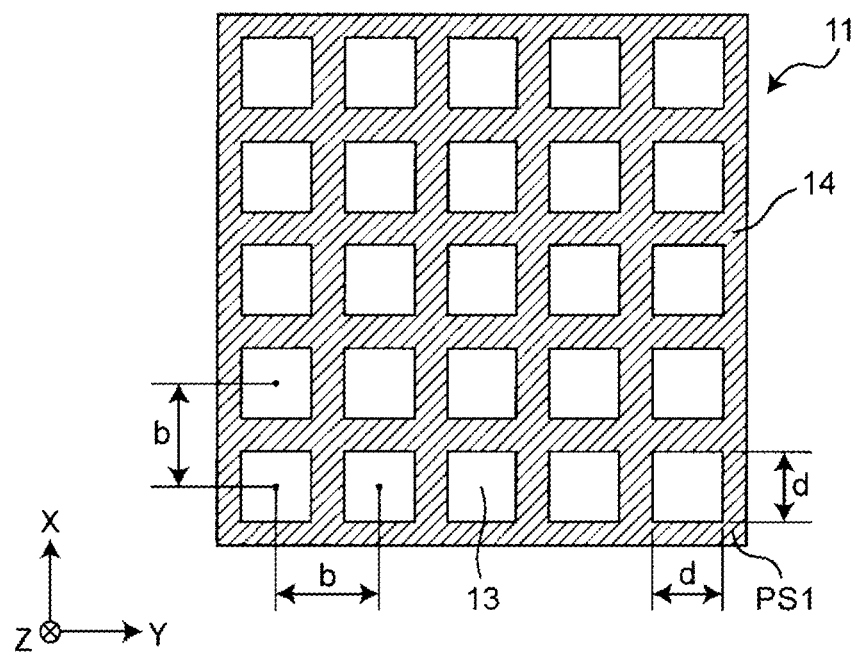
FIG. 5 is a schematic view of part of the filter portion of FIG. 4 when viewed from a thickness direction.

FIG. 4 is an enlarged perspective view of part of the exemplary filter portion 11. FIG. 5 is a schematic view of part of the filter portion 11 of FIG. 4 when viewed from the thickness direction.

As illustrated in FIG. 4 and FIG. 5, the filter portion 11 is a plate-like structural body having a first main surface PS1 by which a filtration object contained in a liquid is captured and a second main surface PS2 facing the first main surface PS1. In the filter portion 11, a plurality of through-holes 13 penetrating through the first main surface PS1 and the second main surface PS2 is formed. Specifically, the plurality of through-holes 13 is formed in a filter base body portion 14 constituting the filter portion 11.

Returning to FIGS. 1 to 3, the shape of the filter portion 11 is, for example, circular, rectangular, or elliptical when viewed from the thickness direction (Z direction) of the filtration filter 10. According to an aspect of the present disclosure, the filter portion 11 has a substantially circular shape. Note that in the present specification, the term "substantially circular shape" may mean that the ratio of the length of the major axis to the length of the minor axis is equal to or more than 1.0 and equal to or less than 1.2.

Returning to FIG. 4 and FIG. 5, the plurality of through-holes 13 is periodically disposed on the first main surface PS1 and the second main surface PS2 of the filter portion 11. Specifically, the plurality of through-holes 13 is provided at equal intervals in a matrix shape in the filter portion 11.

According to an aspect of the present disclosure, the through-hole 13 has a square shape when viewed from the first main surface PS1 side of the filter portion 11, that is, from the Z direction. Note that the shape of the through-hole 13 viewed from the Z direction is not limited to a square shape, and may be a shape such as a rectangle, a circle, an ellipse, or the like, for example.

According to an aspect of the present disclosure, the shape (cross-sectional shape) of the through-hole 13 projected onto a surface perpendicular to the first main surface PS1 of the filter portion 11 is rectangular. Specifically, the cross-sectional shape of the through-hole 13 is a rectangular shape in which the length of one side in the radial direction of the filtration filter 10 is longer than the length of one side in the thickness direction of the filtration filter 10. Note that the cross-sectional shape of the through-hole 13 is not limited to a rectangular shape, and may be, for example, a parallelogram, a tapered shape such as a trapezoid or the like, a symmetrical shape, or an asymmetric shape.

According to an aspect of the present disclosure, the plurality of through-holes 13 is provided at equal intervals in two arrangement directions parallel to the respective sides of the square shape when viewed from the first main surface PS1 side (Z direction) of the filter portion 11, that is, in the X direction and the Y direction in FIG. 4. As described above, providing the plurality of through-holes 13 in a square lattice arrangement makes it possible to increase an opening ratio, and to reduce a resistance of the filtration filter 10 to a liquid passing therethrough. This configuration makes it possible to shorten filtration time and to reduce stress on a filtration object.

Note that the arrangement of the plurality of through-holes 13 is not limited to the square lattice arrangement, and may be, for example, a quasi-periodic arrangement or a periodic arrangement. Examples of the periodic arrangement may include, as long as a quadrangular arrangement, a rectangular arrangement in which the intervals in the two arrangement directions are not equal to each other, or may be a triangular lattice arrangement, a regular triangular lattice arrangement, or the like. Note that it is sufficient that the plurality of through-holes 13 is provided in the filter portion 11, and the arrangement thereof is not limited.

The interval of the plurality of through-holes 13 is appropriately designed in accordance with the type (size, form, property, elasticity) or amount of cells which are filtration objects. Here, as illustrated in FIG. 5, the interval between the through-holes 13 means a distance b between the center of an arbitrary through-hole 13 and the center of the adjacent through-hole 13 when the through-hole 13 is viewed from the first main surface PS1 side of the filter portion 11. In the case of the structural body of the periodic arrangement, the interval b between the through-holes 13 is, for example, greater than one time and equal to or smaller than 10 times the length of one side d of the through-hole 13, and is preferably equal to or smaller than three times the length of the one side d of the through-hole 13. Alternatively, for example, the opening ratio of the filter portion 11 is equal to or greater than 10%, and the opening ratio is preferably equal to or greater than 25%. This configuration makes it possible to reduce the resistance of the filter portion 11 to the liquid passing there through. Accordingly, the processing time can be shortened, and stress on the cells can be reduced. Note that the opening ratio is calculated by (the area occupied by the through-holes 13)/(the projected area of the first main surface PS1 when assuming that the through-holes 13 are not provided).

The thickness of the filter portion 11 is preferably greater than 0.1 times and equal to or smaller than 100 times the size (one side d) of the through-hole 13. More preferably, the thickness of the filter portion 11 is greater than 0.5 times and equal to or smaller than 10 times the size (one side d) of the through-hole 13. This configuration makes it possible to reduce the resistance of the filtration filter 10 to the liquid, and makes it possible to shorten the filtration time. As a result, stress on the filtration object can be reduced.

In the filter portion 11, it may be preferable that the first main surface PS1 with which the liquid containing the filtration object comes into contact have a small surface roughness. Here, the surface roughness means an average value of differences between the maximum value and the minimum value measured by a stylus type step profiler at five arbitrary points on the first main surface PS1. According to an aspect of the present disclosure, the surface roughness is preferably smaller than the size of the filtration object, and is more preferably smaller than half the size of the filtration object. In other words, the openings of the plurality of through-holes 13 on the first main surface PS1 of the filter portion 11 are formed on the same plane (XY plane). Furthermore, the filter base body portion 14, which is a portion of the filter portion 11 where the through-holes 13 are not formed, is continuously and integrally formed. This configuration reduces adhesion of the filtration object to the surface (first main surface PS1) of the filter portion 11, and makes it possible to reduce the resistance of the liquid.

The opening on the first main surface PS1 side and the opening on the second main surface PS2 side of each through-hole 13 communicate with each other through a continuous wall surface. Specifically, the through-hole 13 is provided such that the opening on the first main surface PS1 side can be projected onto the opening on the second main surface PS2 side. That is, when the filter portion 11 is viewed from the first main surface PS1 side, the through-hole 13 is provided such that the opening on the first main surface PS1 side overlaps with the opening on the second main surface PS2 side. According to an aspect of the present disclosure, the through-hole 13 is provided such that the inner wall thereof is perpendicular to the first main surface PS1 and the second main surface PS2.

The material forming the filter base body portion 14 contains a metal and/or a metal oxide as a main component. The filter base body portion 14 may be made of, for example, gold, silver, copper, platinum, nickel, palladium, titanium, an alloy thereof, or an oxide thereof. In particular, by using titanium or a nickel-palladium alloy, elution of the metal is reduced, and thus the influence on the filtration object can be reduced.

The frame portion 12 is a member disposed so as to surround the outer periphery of the filter portion 11. The frame portion 12 is formed in a ring shape when viewed from the first main surface PS1 side of the filter portion 11. Furthermore, when the filtration filter 10 is viewed from the first main surface PS1 side, the center of the frame portion 12 coincides with the center of the filter portion 11. That is, the frame portion 12 is formed concentrically with the filter portion 11.

The frame portion 12 functions as a connection portion that connects the filtration filter 10 and the holder 20.

Furthermore, on the frame portion 12, information (for example, the dimension of the through-hole 13, and the like) of the filter may be displayed. This makes it easier to grasp the dimension of the filter hole without performing the length measurement or the like again and to distinguish the front and back sides from each other.

According to an aspect of the present disclosure, the filtration filter 10 has a diameter of 25 mm and a film thickness of 1.8 μm. The diameter of the filter portion 11 is 20 mm, and the width of the frame portion 12 is 2.5 mm. The filtration filter 10 is not limited to these dimensions, and may be manufactured in other dimensions.

According to an aspect of the present disclosure, the material forming the frame portion 12 is the same as the material forming the filter portion 11 (filter base body portion 14). Note that the material of the frame portion 12 and the material of the filter portion 11 need not be the same, and may be different from each other. In addition, the material of the frame portion 12 and the filter portion 11 need not be formed integrally with each other, and may be constituted of other members.

Returning to FIGS. 1 to 3, the holder 20 has an introduction port 20a for introducing a liquid, a discharge port 20b for discharging the liquid, and a flow path 20c for communicating the introduction port 20a and the discharge port 20b with each other. The holder 20 holds the filtration filter 10 in the flow path 20c between the introduction port 20a and the discharge port 20b. According to an aspect of the present disclosure, the holder 20 holds the filtration filter 10 above the discharge port 20b in the flow path 20c.

The holder 20 is formed of, for example, a material such as polyoxymethylene, polyether ether ketone, or the like.

The holder 20 is formed in a tubular shape. Specifically, in the holder 20, the introduction port 20a and the discharge port 20b are provided so as to face each other. In the inside of the holder 20, the flow path 20c is provided so as to communicate the introduction port 20a and the discharge port 20b with each other.

According to an aspect of the present disclosure, the holder 20 has a tubular first holder 21 and a tubular second holder 22 disposed in the inner side portion of the first holder 21.

The first holder 21 forms an outer wall of the holder 20 and one end side of the holder 20 at which the discharge port 20b is provided. In the inside of the first holder 21, a projection portion 21a for holding the filtration filter 10 is formed. The projection portion 21a is provided so as to project from the inner wall of the first holder 21 toward the inner side portion of the first holder 21. Specifically, the projection portion 21a is formed in a ring shape in the first holder 21.

More specifically, the first holder 21 includes a tubular first main body portion 21aa that has a first end portion E1 located on the introduction port 20a side of the holder 20 and a second end portion E2 located on the discharge port 20b side of the holder 20.

According to an aspect of the present disclosure, the projection portion 21a is formed in a lower portion of the first holder 21. In other words, the projection portion 21a is formed at the one end of the holder 20 at which the discharge port 20b is provided. More specifically, the projection portion 21a is provided at the second end portion E2 of the first main body portion 21aa. The projection portion 21a functions as a pedestal on which the filtration filter 10 is placed. With this configuration, the filtration filter 10 is disposed at a position above the discharge port 20b and closer to the discharge port 20b than the introduction port 20a of the holder 20.

The height of the projection portion 21a is set to be equal to or greater than 0.01 times and smaller than two times the height of the holder 20. Since the lower the height of the projection portion 21a is, the smaller the amount of the liquid for recovery may be required, the height of the projection portion 21a is preferably set to be equal to or greater than 0.1 times and equal to or smaller than 0.5 times the height of the holder 20. The height of the projection portion 21a means the length from an end surface on the one end side of the holder 20 at which the discharge port 20b is provided to an upper surface of the projection portion 21a.

The frame portion 12 of the filtration filter 10 is placed on the upper surface of the projection portion 21a. Accordingly, a holding position of the filtration filter 10 is determined by the position where the projection portion 21a is formed. In other words, the holding position of the filtration filter 10 can be changed by changing the position at which the projection portion 21a is formed.

According to an aspect of the present disclosure, the filtration filter 10 is disposed so as to be substantially perpendicular to the inner wall of the holder 20. In the present specification, the term "substantially perpendicular" may mean a range of equal to or greater than 80° and equal to or smaller than 100°. This makes it possible to dispose the first main surface PS1 and the second main surface PS2 of the filtration filter 10 so as to be substantially perpendicular to the direction in which a liquid 50 flows.

A lower surface of the first holder 21 is configured so as to make surface contact with a flat surface. The lower surface of the first holder 21 means the end surface on the one end side of the holder 20 at which the discharge port 20b is provided. That is, the lower surface of the first holder 21 means an end surface of the second end portion E2 of the first main body portion 21aa. The lower surface of the first holder 21 has a flat shape. In the present specification, the term "flat shape" may mean a shape in which, when the first holder 21 is placed on a horizontal surface, the entire surface of the lower surface of the first holder 21 makes contact with the horizontal surface.

As described above, the one end of the holder 20 at which the discharge port 20b is provided is configured so as to make surface contact with the flat surface. This makes it possible, when the filtration recovery device 1A is disposed on the flat surface, to suppress the leakage of the liquid from the filtration recovery device 1A.

It may be preferable that the gravity of the entire filtration recovery device 1A be greater than the buoyancy with respect to a filtration solution, a filtration recovery solution, and a washing liquid. With this configuration, the filtration recovery device 1A does not float in the liquid, installation with a container becomes easy, and therefore the filtration operation is easy to be performed.

The second holder 22 forms an inner wall of the holder 20 and the other end side of the holder 20 at which the introduction port 20a is provided. The second holder 22 is disposed in the inner side portion of the first holder 21, whereby the outer wall of the second holder 22 and the inner wall of the first holder 21 make surface contact with each other. That is, the second holder 22 is fitted into the first holder 21, whereby the outer wall of the second holder 22 and the inner wall of the first holder 21 make surface contact with each other. This improves a sealing performance of the holder 20.

Furthermore, when assembling the filtration recovery device 1A, by inserting the filtration filter 10 in the first holder 21, the filtration filter 10 and the first holder 21 can be aligned with each other. Additionally, since the filtration filter 10 can be fixed to the holder 20 without using an adhesive, it is possible to reduce the number of processes and to reduce the influence on the filtration object.

Furthermore, by the second holder 22 being disposed in the inner side portion of the first holder 21, the frame portion 12 of the filtration filter 10 is held between the one end of the second holder 22 and the projection portion 21a of the first holder 21. This makes it possible to hold the filtration filter 10 in the flow path 20c.

More specifically, the second holder 22 includes a tubular second main body portion 22aa that has a third end portion E3 located on the introduction port 20a side of the holder 20 and a fourth end portion E4 located on the discharge port 20b side of the holder 20. In the holder 20, an inner wall of the first main body portion 21aa and an outer wall of the second main body portion 22aa make surface contact with each other. The frame portion 12 of the filtration filter 10 is held between the fourth end portion E4 of the second main body portion 22aa and the upper surface of the projection portion 21a.

According to an aspect of the present disclosure, holes 24 are provided in the outer surface of the holder 20. Specifically, the two circular holes 24 are provided in the outer surface of the first holder 21. The two holes 24 are face each other. The holes 24 are each formed of, for example, a through-hole. Providing the holes 24 in the outer surface of the first holder 21 makes it easy to detach the second holder 22 from the first holder 21. Furthermore, the holes 24 can be used for alignment when the second holder 22 is fitted into the first holder 21. Furthermore, part of a container can be attached to the hole 24 during filtration. Furthermore, providing the holes 24 makes it possible to alleviate expansion and contraction of the resin due to a temperature change and the like, and to suppress breakage and deterioration in fittability of the holder 20. Furthermore, frictional resistance between the first holder 21 and the second holder 22 can be reduced by the holes 24, and the second holder 22 can be easily detached from the first holder 21. Note that the hole 24 is not limited to the through-hole, and may be a non-through-hole. The non-through-hole is formed by recessing the outer surface of the first holder 21. In addition, the number of holes 24 is not limited to two, and one or a plurality of holes 24 may be provided. The shape of the hole 24 is not limited to a circle, and may be a shape other than the circle, for example, a quadrangle or the like.

Figure 6:
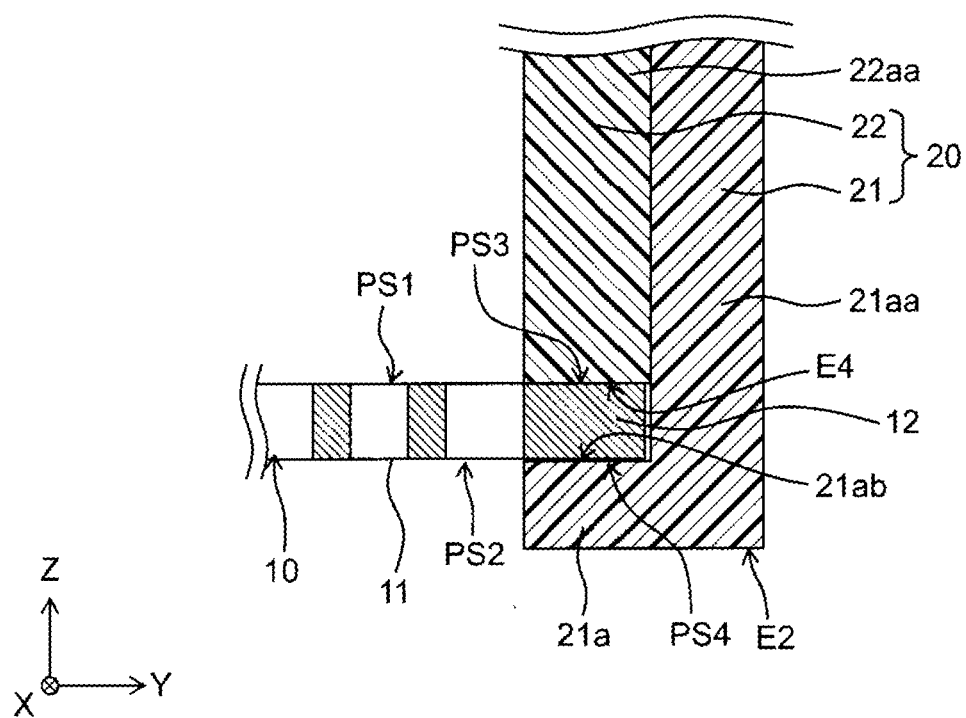
FIG. 6 is a schematic enlarged view of a portion of the filtration recovery device of FIG. 3.

FIG. 6 is a schematic enlarged view of a portion of the filtration recovery device of FIG. 3. As illustrated in FIG. 6, the frame portion 12 of the filtration filter 10 is held by the projection portion 21a of the first holder 21 and the one end of the second holder 22.

Specifically, the projection portion 21a of the first holder 21 and the one end of the second holder 22 hold the frame portion 12 of the filtration filter 10 in the thickness direction (Z direction) therebetween. Furthermore, the frame portion 12 of the filtration filter 10 is held by the projection portion 21a of the first holder 21 and the one end of the second holder 22 in a state of continuously extending in directions (X and Y directions) from the filter portion 11 toward the frame portion 12.

The expression "held by the projection portion 21a of the first holder 21 and the one end of the second holder 22 in a state of continuously extending in directions (X and Y directions) from the filter portion 11 toward the frame portion 12" means that, in the frame portion 12 of the filtration filter 10, a portion extending in the directions (X and Y directions) from the filter portion 11 toward the frame portion 12 is held by the projection portion 21a of the first holder 21 and the one end of the second holder 22 without bending. In other words, the expression means that the portion of the frame portion 12 held by the projection portion 21a of the first holder 21 and the one end of the second holder 22 is not bent.

As described above, by the second holder 22 being fitted into the first holder 21, the frame portion 12 of the filtration filter 10 is held by the projection portion 21a of the first holder 21 and the one end of the second holder 22. More specifically, the frame portion 12 of the filtration filter 10 is held between the fourth end portion E4 of the second main body portion 22aa of the second holder 22 and an upper surface 21ab of the projection portion 21a of the first holder 21.

On the upper surface 21ab of the projection portion 21a of the first holder 21 and on the fourth end portion E4 of the second main body portion 22aa of the second holder 22, a member having elastic force or frictional force may be disposed. This makes it easy to perform holding regardless of the thickness of the filtration filter 10. Furthermore, detachment of the filtration filter 10 from the holder 20 during the operation may be suppressed.

On the upper surface 21ab of the projection portion 21a of the first holder 21 and on the fourth end portion E4 of the second main body portion 22aa of the second holder 22, a member having elastic force or frictional force may be disposed. This makes it easy to perform holding regardless of the thickness of the filtration filter 10. Furthermore, detachment of the filtration filter 10 from the holder 20 during the operation may be suppressed.

The frame portion 12 has a first surface PS3 that makes contact with the one end of the second holder 22, and a second surface PS4 that makes contact with the projection portion 21a of the first holder 21. The first surface PS3 of the frame portion 12 is located on the same side as the first main surface PS1 of the filter portion 11, and the second surface PS4 of the frame portion 12 is located on the same side as the second main surface PS2 of the filter portion 11. According to an aspect of the present disclosure, the first surface PS3 and the second surface PS4 of the frame portion 12 are face each other and are each formed flat without bending.

The frame portion 12 has a first surface PS3 that makes contact with the one end of the second holder 22, and a second surface PS4 that makes contact with the projection portion 21a of the first holder 21. The first surface PS3 of the frame portion 12 is located on the same side as the first main surface PS1 of the filter portion 11, and the second surface PS4 of the frame portion 12 is located on the same side as the second main surface PS2 of the filter portion 11. According to an aspect of the present disclosure, the first surface PS3 and the second surface PS4 of the frame portion 12 are face each other and are each formed flat without bending.

The one end of the second holder 22 has an end surface formed flat, and makes contact with the first surface PS3 of the frame portion 12. The upper surface of the projection portion 21a of the first holder 21 is formed flat, and makes contact with the second surface PS4 of the frame portion 12.

According to an aspect of the present disclosure, the frame portion 12 of the filtration filter 10 is held between the projection portion 21a of the first holder 21 and the one end of the second holder 22 throughout the entire circumference. Furthermore, the frame portion 12 is held between the projection portion 21a of the first holder 21 and the one end of the second holder 22 in a state of continuously extending in the directions (X and Y directions) from the filter portion 11 toward the frame portion 12. In other words, the projection portion 21a of the first holder 21 and the one end of the second holder 22 hold the frame portion 12 in the thickness direction there between without causing to bend. This configuration makes it possible to hold the filtration filter 10 in the flow path 20c of the holder 20 in a state where pulling force toward an outer side portion in the radial direction of the filtration filter 10 is suppressed. As a result, breakage of the filtration filter 10 during the filtration may be suppressed.

The second holder 22 has a flange 22a and a handle 22b. The flange 22a is formed at an upper portion of the second holder 22. The flange 22a extends toward an outer side portion of the second holder 22 at the upper portion of the second holder 22. Specifically, the flange 22a is formed in a ring shape at the upper portion of the second holder 22.

Figure 7:
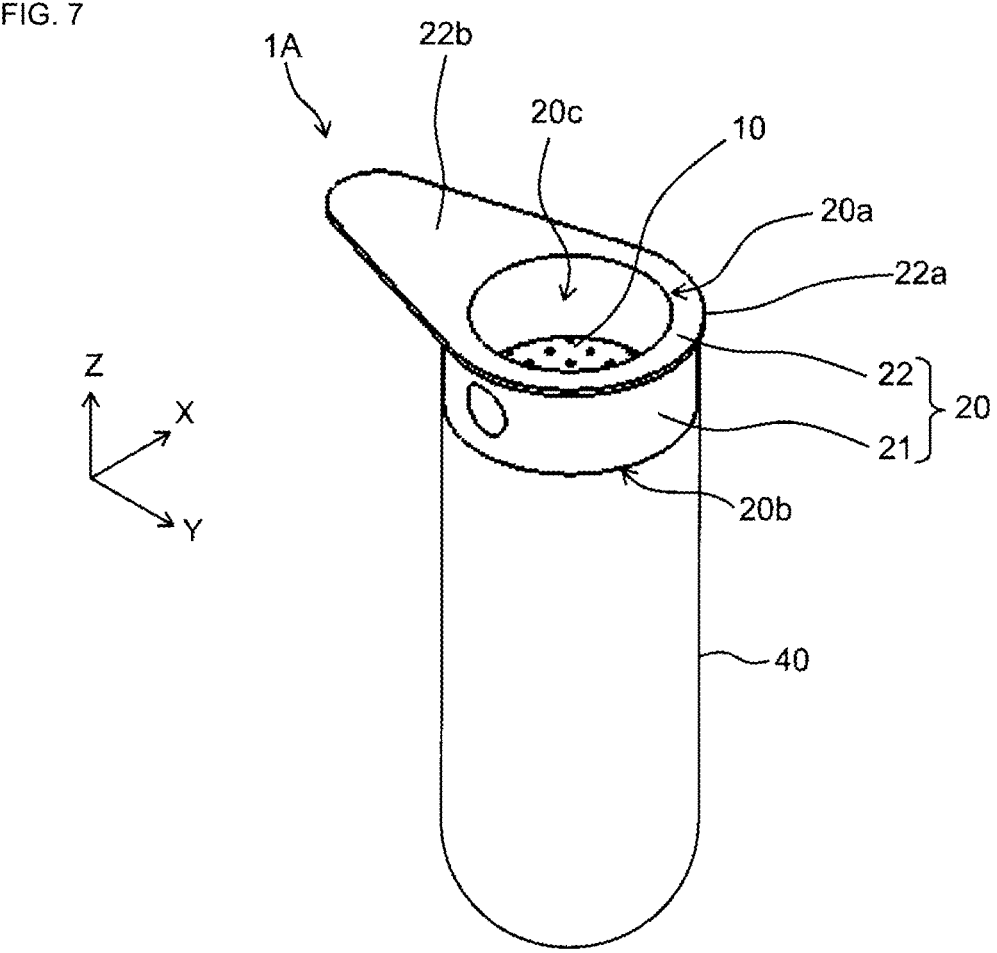
FIG. 7 is a schematic view illustrating a state in which the filtration recovery device in accordance with aspects of the present disclosure is attached to a centrifuge tube.

FIG. 7 is a schematic view illustrating a state in which the filtration recovery device 1A according to an aspect of the present disclosure is attached to a centrifuge tube 40. As illustrated in FIG. 7, the filtration recovery device 1A can be attached to, for example, the centrifuge tube 40 by the second holder 22 having the flange 22a. Specifically, in the case where the filtration recovery device 1A is attached to an opening of the centrifuge tube 40, the flange 22a is placed on an opening end portion defining the opening of the centrifuge tube 40. As described above, the flange 22a is supported by the opening end portion of the centrifuge tube 40.

The handle 22b is formed at the upper portion of the second holder 22. The handle 22b extends from the flange 22a toward the outer side portion of the second holder 22. Providing the handle 22b in the second holder 22 makes it easy to handle the filtration recovery device 1A.

Figure 8:
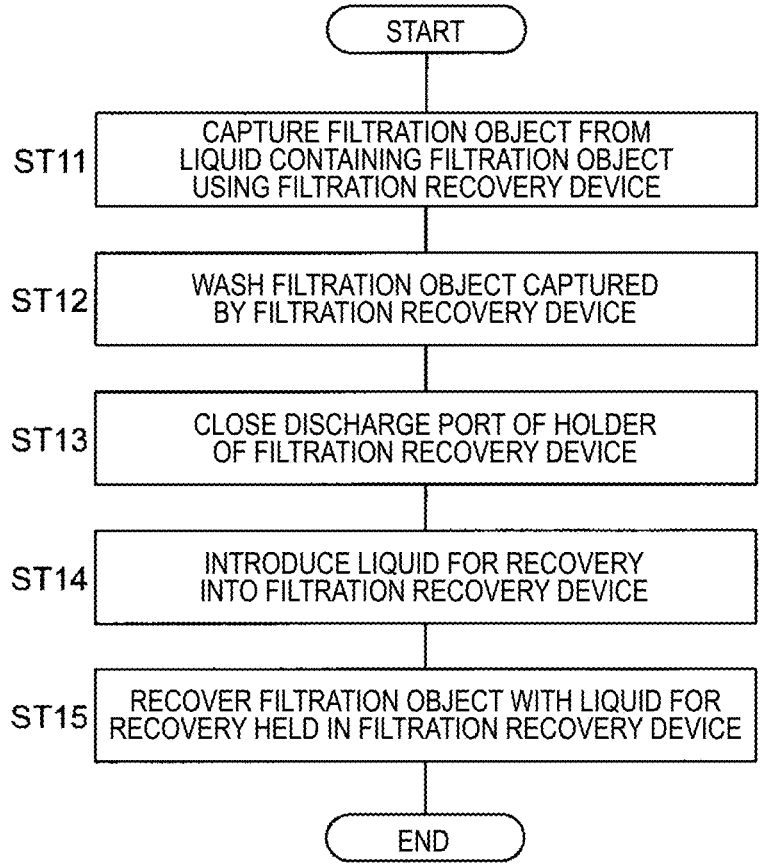
FIG. 8 is a flowchart of an example of a filtration recovery method in accordance with aspects of the present disclosure.

An example of a filtration recovery method will be described with reference to FIG. 8 and FIGS. 9A to 9E. FIG. 8 illustrates a flowchart of an example of a filtration recovery method according to an aspect of the present disclosure. FIGS. 9A to 9E illustrate an example of a process of the filtration recovery method according to an aspect of the present disclosure. Note that the filtration recovery method means a method of filtering a liquid containing a filtration object by using the filtration recovery device 1A, and recovering the filtration object.

Figure 9A:
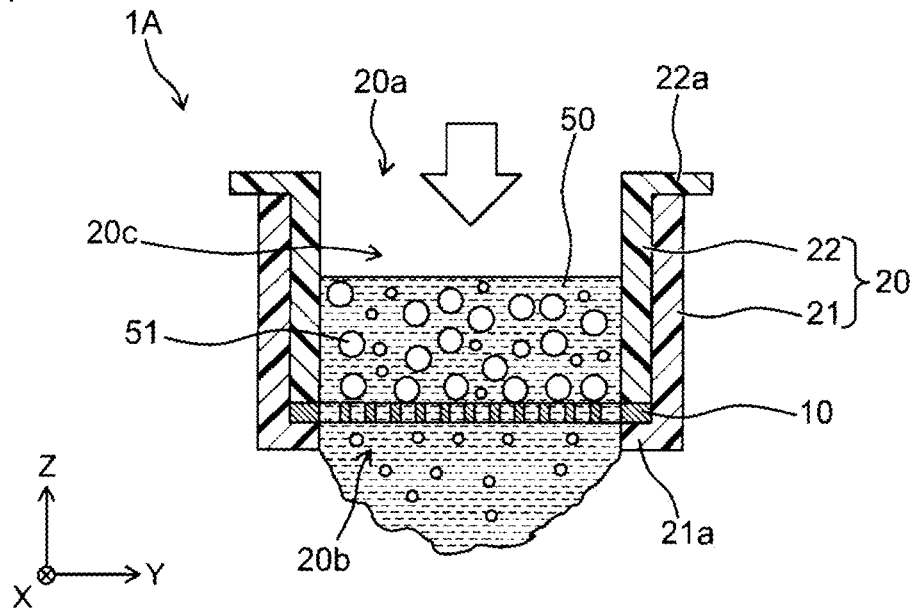
FIG. 9A is a diagram illustrating an example of a process of the filtration recovery method in accordance with aspects of the present disclosure.

As illustrated in FIG. 8 and FIG. 9A, in step ST11, the liquid 50 containing a filtration object 51 is filtered by using the filtration recovery device 1A, whereby the filtration object 51 is captured by the filtration filter 10. Specifically, the filtration recovery device 1A is attached to the centrifuge tube 40 (see FIG. 7), and the liquid 50 containing the filtration object 51 is introduced from the introduction port 20a of the holder 20 of the filtration recovery device 1A into the flow path 20c inside the holder 20. Note that in FIG. 9A, illustration of the centrifuge tube 40 is omitted.

Figure 9B:
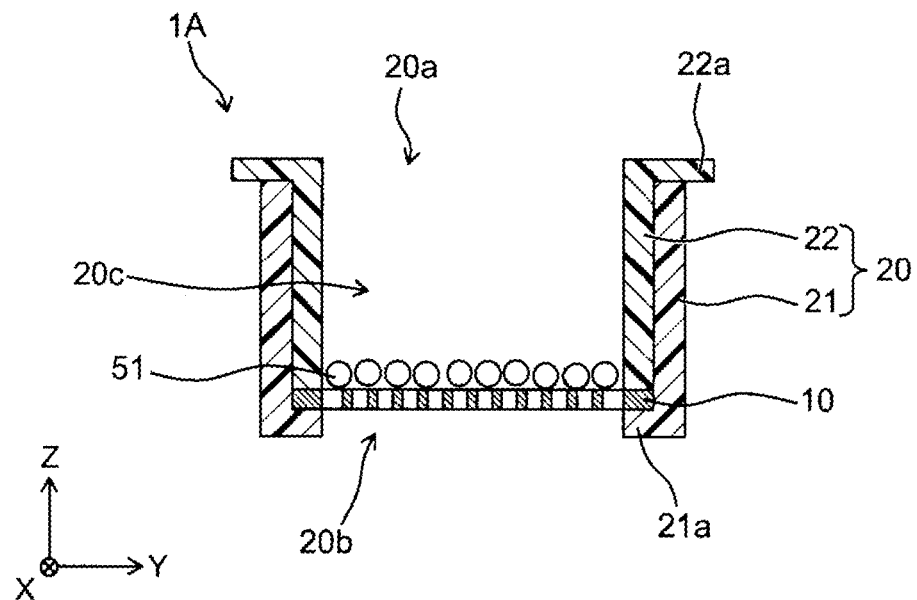
FIG. 9B is a diagram illustrating an example of a process of the filtration recovery in accordance with aspects of the present disclosure.

The liquid 50 containing the filtration object 51 passes through the filtration filter 10 disposed in the flow path 20c, and is discharged from the discharge port 20b. As a result, as illustrated in FIG. 9B, the filtration object 51 larger than the through-hole 13 is captured on the first main surface PS1 of the filtration filter 10.

In step ST12, the filtration object 51 captured by the filtration recovery device 1A is washed. Specifically, a washing liquid is introduced to the filtration filter 10, and the filtration object 51 is washed.

Figure 9C:
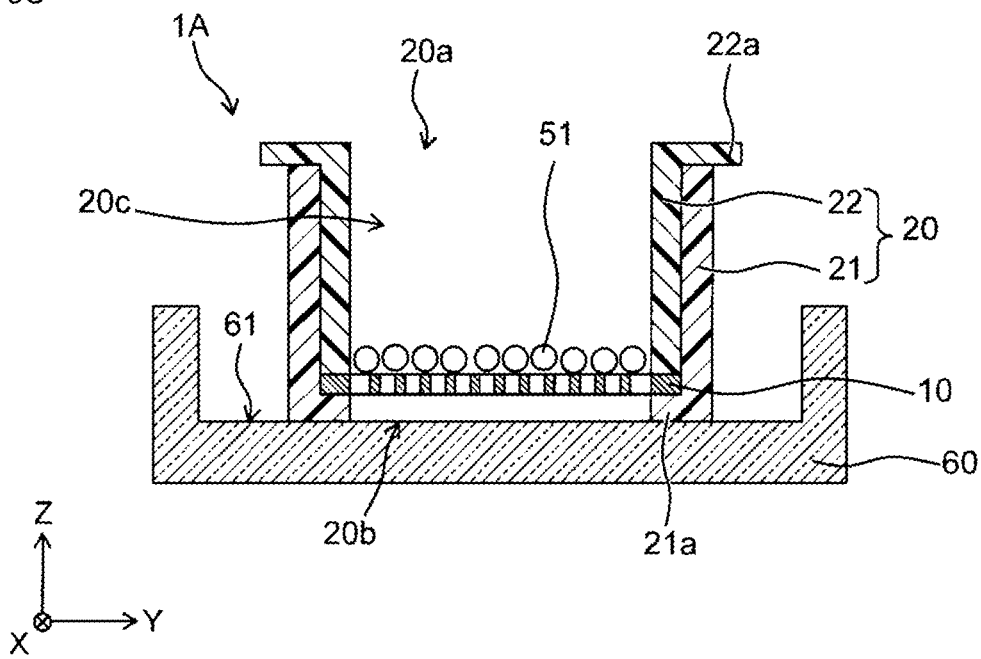
FIG. 9C is a diagram illustrating an example of a process of the filtration recovery in accordance with aspects of the present disclosure.

In step ST13, the discharge port 20b of the holder 20 of the filtration recovery device 1A is closed. For example, as illustrated in FIG. 9C, the filtration recovery device 1A is disposed on a petri dish 60. Specifically, the one end of the holder 20 of the filtration recovery device 1A at which the discharge port 20b is provided is placed on a bottom surface portion 61 of the petri dish 60. The bottom surface portion 61 of the petri dish 60 is formed in a flat shape, and therefore makes surface contact with the end surface on the one end side of the holder 20 at which the discharge port 20b is provided. Note that as described above, the end surface on the one end side of the holder 20 at which the discharge port 20b is provided is formed in a flat shape. With this configuration, a state where the discharge port 20b is closed by the bottom surface portion 61 of the petri dish 60 is obtained. That is, a state where the discharge port 20b is sealed by the bottom surface portion 61 of the petri dish 60 may be obtained.

Figure 9D:
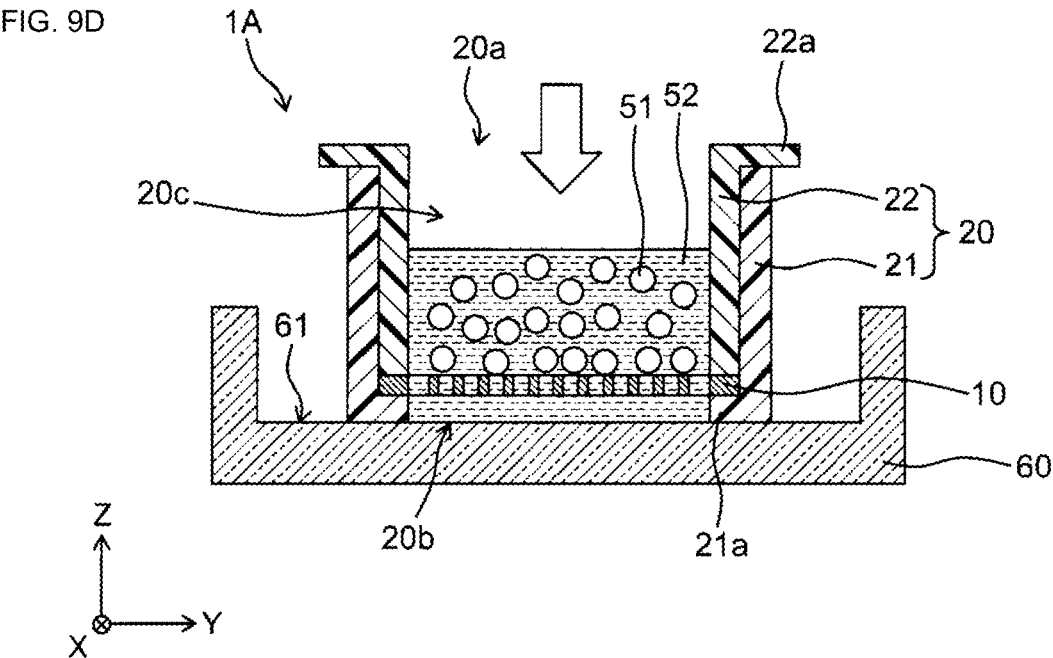
FIG. 9D is a diagram illustrating an example of a process of the filtration recovery in accordance with aspects of the present disclosure.

In step ST14, a liquid 52 for recovery (hereinafter, referred to as "liquid 52") is introduced into the filtration recovery device 1A. As illustrated in FIG. 9D, the liquid 52 is introduced from the introduction port 20a of the holder 20. Since the discharge port 20b of the holder 20 is in a closed state through step ST13, the liquid 52 is held in the flow path 20c inside the holder 20.

As a result, the filtration object 51 is released from the filtration filter 10 and floats in the liquid 52 held inside the holder 20. Note that the state where the discharge port 20b of the holder 20 is closed refers to a state where leakage of the liquid 52 is suppressed, and need not be a state where leakage of the liquid 52 is completely prevented. It is sufficient that the liquid 52 of a liquid amount of a degree capable of recovering the filtration object 51 can be held in the flow path 20c inside the holder 20. That is, in the filtration recovery device 1A, in the state where the discharge port 20b of the holder 20 is closed, the leakage of the liquid 52 of a degree not affecting the recovery may be allowed.

Figure 9E:
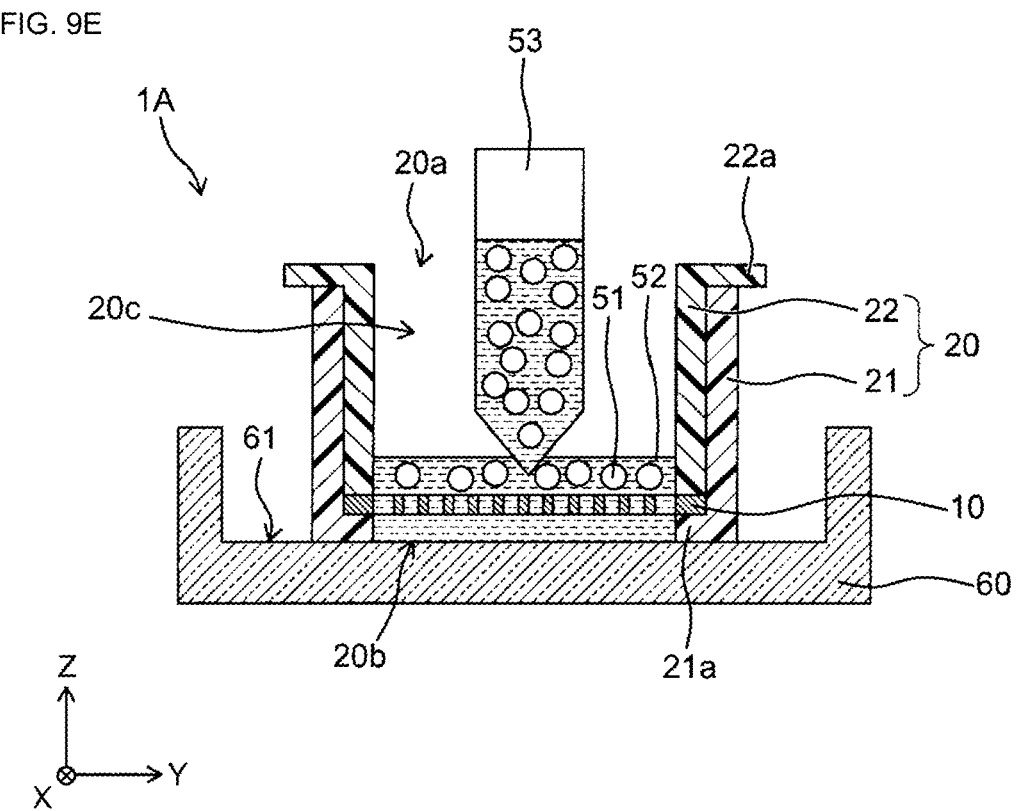
FIG. 9E is a diagram illustrating an example of a process of the filtration recovery in accordance with aspects of the present disclosure.

In step ST15, the filtration object 51 is recovered together with the liquid 52 held in the filtration recovery device 1A. As illustrated in FIG. 9E, for example, by using a pipette 53, the liquid 52 held in the flow path 20c of the holder 20 is recovered together with the filtration object 51.

As described above, in the filtration recovery method, by executing steps ST11 to ST15, the filtration object 51 can be recovered together with the liquid 52 for recovery.

According to the filtration recovery device 1A and the filtration recovery method according to an aspect of the present disclosure, the following effects may be obtained.

The filtration recovery device 1A includes the filtration filter 10 and the holder 20 having the introduction port 20a, the discharge port 20b, and the flow path 20c that communicates the introduction port 20a and the discharge port 20b with each other. The filtration filter 10 is disposed above the discharge port 20b in the flow path 20c of the holder 20.

According to this configuration, in the filtration recovery device 1A, after the filtration of the liquid 50 containing the filtration object 51 is performed, the filtration object 51 captured by the filtration filter 10 may be easily recovered.

Specifically, the discharge port 20b can be closed when recovering the filtration object 51. This makes it possible to introduce the liquid 52 for recovery from the introduction port 20a of the holder 20, and to hold the liquid 52 in the flow path 20c inside the holder 20. As a result, the filtration object 51 can be easily recovered together with the liquid 52 by the pipette 53.

Furthermore, disposing the filtration filter 10 above the discharge port 20b of the holder 20 makes it possible to easily close the discharge port 20b. For example, in the case where the one end of the holder 20 at which the discharge port 20b is provided is placed on a flat surface, the discharge port 20b can be closed without being affected by the filtration filter 10. Specifically, it is possible to suppress deterioration in the sealing performance between the holder 20 and the flat surface due to undulation or the like of the filtration filter 10.

Furthermore, in the case where the filtration object is a cell, by using a solvent or the like as the liquid 52 for recovery, by recovering the solvent together with the cell, it is possible to easily generate a cell suspension. Additionally, by introducing the liquid for recovery, it is possible to prevent drying and maintain activity of the captured cell. Furthermore, by adjusting an amount of the liquid 52 for recovery introduced into the inside of the filtration recovery device 1A, a liquid amount of the cell suspension to be generated can be easily adjusted. Furthermore, by adjusting the amount of the liquid 52 for recovery introduced into the inside of the filtration recovery device 1A, a concentration of the cell suspension to be recovered can be easily adjusted.

The projection portion 21a provided so as to project toward the inner side portion of the holder 20 is formed on the inner wall of the holder 20, and the projection portion 21a holds the filtration filter 10. This configuration makes it possible to dispose the filtration filter 10 in the flow path 20c between the introduction port 20a and the discharge port 20b of the holder 20.

The projection portion 21a is formed at the one end of the holder 20 at which the discharge port 20b is provided, and the filtration filter 10 is disposed at a position closer to the discharge port 20b than the introduction port 20a. With this configuration, since the filtration filter 10 can be disposed near the discharge port 20b, it is possible to reduce a liquid amount of the liquid 52 may be required for recovery. That is, it is possible to recover the filtration object 51 with a small amount of the liquid 52.

The holder 20 has the tubular first holder 21 having the projection portion 21a and the tubular second holder 22 disposed in the inner side portion of the first holder 21. The filtration filter 10 is held between the projection portion 21a of the first holder 21 and the one end of the second holder 22. This configuration makes it possible to firmly fix the filtration filter 10 to the flow path 20c of the holder 20.

The one end of the holder 20 at which the discharge port 20b is provided is configured so as to make surface contact with the flat surface. With this configuration, when the one end of the holder 20 at which the discharge port 20b is provided is placed on the flat surface, it is possible to easily close the discharge port 20b.

The filtration filter 10 includes the filter portion 11 having at least one of a metal and a metal oxide as a main component and having the plurality of through-holes 13, and the frame portion 12 disposed so as to surround the outer periphery of the filter portion 11. This configuration makes it possible to easily recover the filtration object 51 and improve the recovery rate. For example, in a resin filter or the like, due to variation in dimension and arrangement of the through-holes, the filtration object enters the through-hole in some cases. The filtration filter 10 having at least one of a metal and a metal oxide as a main component is uniformly designed in the dimension and arrangement of the through-holes as compared with the resin filter. Accordingly, in the filtration recovery device 1A, by using the filtration filter 10 having at least one of a metal and a metal oxide as a main component, when the filtration object 51 is recovered, the filtration object 51 is easy to be separated from the filtration filter 10, and the recovery rate can be improved as compared with the resin filter.

In the filtration recovery method, the same effects as the effects of the filtration recovery device 1A described above are obtained.

Note that, according to an aspect of the present disclosure, the example in which the filtration filter 10 is a metal filter has been described, but the configuration is not limited thereto. The filtration filter 10 may be a film-like or sheet-like material capable of filtering out the filtration object contained in the liquid 50.

According to an aspect of the present disclosure, the example in which the filtration recovery device 1A includes the one filtration filter 10 has been described, but the configuration is not limited thereto. The filtration recovery device 1A may include a plurality of filtration filters. In the case where the filtration recovery device 1A includes a plurality of filtration filters, the plurality of filtration filters may be disposed in series in a direction in which the liquid 50 flows. Additionally, the dimensions of the through-holes of the plurality of filtration filters may be different from each other. For example, the plurality of filtration filters may be disposed in series in descending order of the dimension of the through-hole, from the upstream side in the direction in which the liquid 50 flows. This configuration makes it possible to filter out the filtration objects different in size at a time and to recover them.

According to an aspect of the present disclosure, the filtration object 51 has been described as a cell, and the liquid 50 has been described as a cell suspension, but the configuration is not limited thereto.

According to an aspect of the present disclosure, the example in which the holder 20 is constituted of the first holder 21 and the second holder 22 has been described, but the configuration is not limited thereto. In the holder 20, the first holder 21 and the second holder 22 may be integrally formed, or may be formed of two or more parts.

According to an aspect of the present disclosure, the example in which the frame portion 12 of the filtration filter 10 is held between the projection portion 21a of the first holder 21 and the one end of the second holder 22 throughout the entire circumference has been described, but the configuration is not limited thereto. For example, the frame portion 12 may be partially held between the projection portion 21a of the first holder 21 and the one end of the second holder 22. This configuration makes it possible to further suppress the pulling force toward the outer side portion in the radial direction of the filtration filter 10. As a result, breakage of the filtration filter 10 during the filtration can be suppressed.

According to an aspect of the present disclosure, the example in which the second holder 22 includes the flange 22a and the handle 22b has been described, but the configuration is not limited thereto. The flange 22a and the handle 22b may not be essential constituent elements.

According to an aspect of the present disclosure, a flange that extends toward the outer side portion of the holder 20 may be provided at the one end of the holder 20 at which the discharge port 20b is provided. This configuration makes it possible to stably dispose the filtration recovery device 1A.

According to an aspect of the present disclosure, the example in which the filtration recovery device 1A is attached to the centrifuge tube 40 when performing filtration has been described, but the configuration is not limited thereto. When the filtration is performed, the filtration recovery device 1A may be attached to a container, a device, or the like other than the centrifuge tube.

According to an aspect of the present disclosure, the example in which the discharge port 20b of the holder 20 is closed by the bottom surface portion 61 of the petri dish 60 when recovery is performed has been described, but the configuration is not limited thereto. When the recovery is performed, it is sufficient that the leakage of the liquid 52 for recovery from the discharge port 20b of the holder 20 can be suppressed, and any configuration which closes the discharge port 20b may be employed. For example, the discharge port 20b may be closed by a flat surface of a pedestal or the like. Alternatively, the discharge port 20b may be closed not only by the flat surface but by a smooth convex surface.

According to an aspect of the present disclosure, the example in which the filtration recovery method includes step ST12 of washing the filtration object 51 captured by the filtration filter 10 has been described, but the configuration is not limited thereto. In the filtration recovery method, step ST12 may not be an essential configuration.

According to an aspect of the present disclosure, the example in which the filtration recovery method includes step ST13 of closing the discharge port 20b of the holder 20 and step ST14 of introducing the liquid 52 for recovery into the inside of the holder 20 has been described, but the configuration is not limited thereto.

For example, in the filtration recovery method, the filtration recovery device 1A may be disposed on the petri dish 60 storing the liquid 52 for recovery, and the liquid 52 may be introduced into the inside of the holder 20 from the discharge port 20b. Specifically, while turning the one end side of the holder 20 at which the discharge port 20b is provided toward the liquid 52 for recovery stored in the petri dish 60, the filtration recovery device 1A is sunk in the liquid 52. As a result, the liquid 52 enters the inside of the holder 20 from the discharge port 20b. By surface contact of the one end of the holder 20 at which the discharge port 20b is provided with the bottom surface portion 61 of the petri dish 60, the discharge port 20b is closed, and the liquid 52 is held inside the holder 20. This configuration also makes it possible to easily recover the filtration object 51.

According to an aspect of the present disclosure, the example of the filtration recovery method in which the filtration object 51 captured by the filtration recovery device 1A is recovered has been described, but the configuration is not limited thereto. For example, in the filtration recovery method, the liquid 50 and an object that have passed through the filtration filter 10 of the filtration recovery device 1A may be recovered. In the case where the filtration recovery device 1A is attached to a container such as the centrifuge tube 40 or the like, the liquid 50 and the object that have passed through the filtration filter 10 accumulate over the bottom of the centrifuge tube 40. The filtration recovery device 1A may be detached from the centrifuge tube 40, and the liquid 50 and the object accumulating inside the centrifuge tube 40 may be recovered.

According to an aspect of the present disclosure, the example in which the filtration filter 10 is disposed so as to be substantially perpendicular to the inner wall of the holder 20 has been described, but the configuration is not limited thereto. The filtration filter 10 may be disposed obliquely with respect to the inner wall of the holder 20.

According to an aspect of the present disclosure, the filtration recovery device 1A and the filtration recovery method have been described, but the configuration is not limited thereto. For example, a kit, which includes the filtration recovery device 1A, for carrying out the filtration method may be used.

Figure 10:
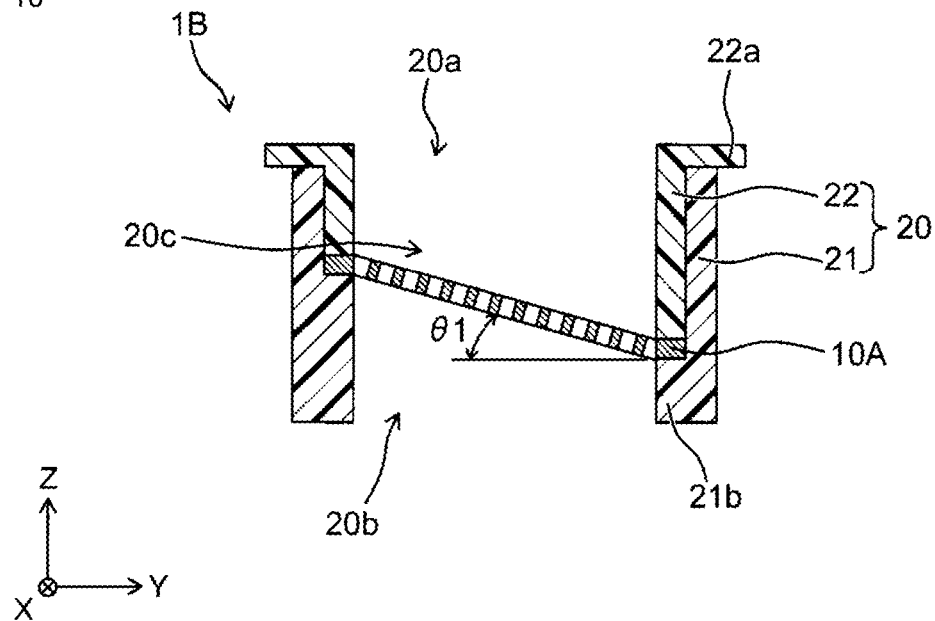
FIG. 10 is a schematic configuration diagram of a filtration recovery device of a modification in accordance with aspects of the present disclosure.

FIG. 10 is a schematic configuration diagram of a filtration recovery device 1B of a modification according to an aspect of the present disclosure. As illustrated in FIG. 10, a filtration filter 10A may be disposed obliquely with respect to the inner wall of the holder 20. Specifically, by changing the height of a projection portion 21b of the first holder 21 along the inner wall of the holder 20, the filtration filter 10A is disposed obliquely with respect to the inner wall of the holder 20.

For example, in a cross section of the filtration recovery device 1B taken by cutting along the YZ plane, the height of the projection portion 21b on the left side is made higher than the height of the projection portion 21b on the right side. As a result, it is possible to dispose the filtration filter 10A so as to be tilted at an angle θ1 with respect to the inner wall of the holder 20. The tilt angle θ1 of the filtration filter 10A is set to, for example, equal to or greater than 10° and equal to or smaller than 80°.

This configuration makes it possible to easily collect the filtration object 51, and it is therefore possible to more easily perform recovery.

A filtration recovery device of according to an aspect of the present disclosure will be described.

According to an aspect of the present disclosure, points different from those in described above will be mainly described. According to an aspect of the present disclosure, the same or equivalent configurations as those described above will be described with the same reference numerals. In addition, According to an aspect of the present disclosure, descriptions overlapping with those described above will be omitted.

Aspects described below are different from those described above, in a point that a liquid amount indication portion is provided in or on the inner wall of the holder.

Figure 11:
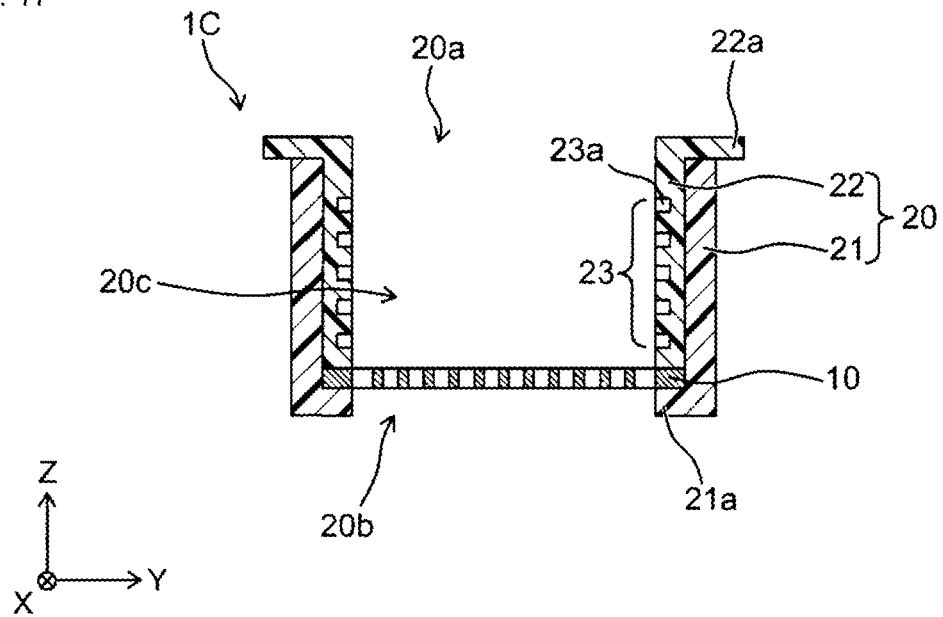
FIG. 11 is a schematic configuration diagram of an example of a filtration recovery device in accordance with aspects of the present disclosure.

FIG. 11 is a schematic configuration diagram of an example of a filtration recovery device 1C according to an aspect of the present disclosure. As illustrated in FIG. 11, in the filtration recovery device 1C, in or on the inner wall of the holder 20, a liquid amount indication portion 23 for indicating a liquid amount of the liquid 52 held inside the holder 20 in a state where the discharge port 20b is closed is provided.

The liquid amount indication portion 23 functions as a scale for indicating the liquid amount of the liquid 52 for recovery held in the flow path 20c inside the holder 20. For example, in the case where the filtration object 51 is a cell and it is desired to generate a desired liquid amount of a cell suspension at the time of recovery, the user introduces the liquid 52 for recovery into the inside of the holder 20 of the filtration recovery device 1C by using the liquid amount indication portion 23 as a reference. Specifically, the liquid 52 is introduced into the inside of the holder 20 until the liquid surface of the liquid 52 held inside the holder 20 reaches the liquid amount indication portion 23 indicating the desired liquid amount. This makes it possible to generate the desired liquid amount of the cell suspension at the time of recovery.

According to an aspect of the present disclosure, the liquid amount indication portion 23 is formed by a plurality of grooves 23a. The plurality of grooves 23a is each provided in a ring shape in or on the inner wall of the holder 20. The plurality of grooves 23a is sequentially provided in the height direction of the filtration recovery device 1C.

According to the filtration recovery device 1C According to an aspect of the present disclosure, the following effects can be obtained.

In the filtration recovery device 1C, in or on the inner wall of the holder 20, the liquid amount indication portion 23 for indicating the liquid amount of the liquid 52 held inside the holder 20 in a state where the discharge port 20b is closed is provided. With this configuration, the user can easily check the liquid amount of the liquid 52 held inside the holder 20. This makes it possible to easily adjust the liquid amount of the liquid 52 may be required for the recovery.

Furthermore, in the case where the filtration object 51 is a cell, it is possible to easily adjust the liquid 52 may be required for generating a desired liquid amount of the cell suspension based on the liquid amount indication portion 23.

Furthermore, by adjusting the liquid amount of the liquid 52 based on the liquid amount indication portion 23, a concentration of the cell suspension can also be adjusted. As a result, it is possible to omit a concentration adjustment process, a redispersion process, or the like of adjusting the cell suspension so as to have the desired concentration after the recovery.

Note that according to an aspect of the present disclosure, the example in which the liquid amount indication portion 23 is formed by the plurality of grooves 23a has been described, but the configuration is not limited thereto. It is sufficient that the liquid amount indication portion 23 has one or the plurality of grooves 23a.

Furthermore, it is sufficient that the liquid amount indication portion 23 functions as a scale by which the liquid amount of the liquid 52 held inside the holder 20 can be checked. For example, the liquid amount indication portion 23 may also be one or a plurality of recessed portions, one or a plurality of protruding portions, one or a plurality of characters, or a combination thereof.

Furthermore, a filtration recovery method may be carried out by using the filtration recovery device 1C. In the filtration recovery method using the filtration recovery device 1C, step ST14 in the filtration recovery method of an aspect of the present disclosure may include introducing the liquid 52 for recovery based on the liquid amount indication portion 23. This configuration makes it possible to adjust the liquid amount of the liquid 52 recovered with the filtration object 51.

A filtration recovery device according to an aspect of the present disclosure will be described.

According to an aspect of the present disclosure, points different from those in described above will be mainly described. According to an aspect of the present disclosure, the same or equivalent configurations as those described above will be described with the same reference numerals.

In addition, according to an aspect of the present disclosure, descriptions overlapping with those described above will be omitted.

Aspects described below different from aspects described above in a point that a petri dish is provided.

Figure 12:
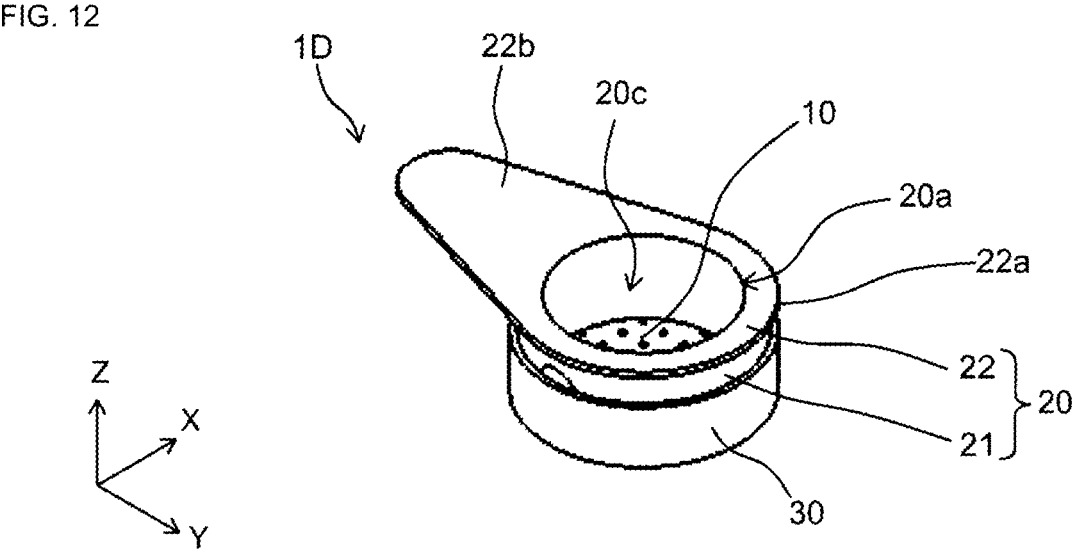
FIG. 12 is a schematic perspective view of an example of a filtration recovery device in accordance with aspects of the present disclosure.
Figure 13:
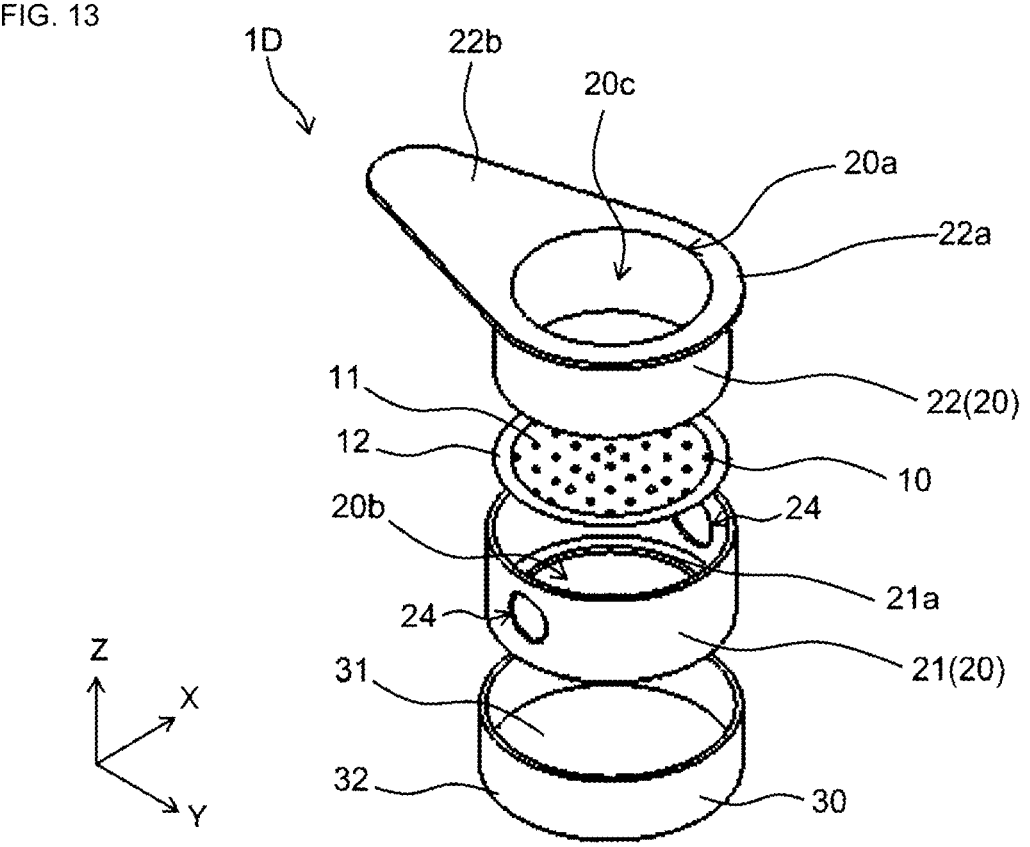
FIG. 13 is a schematic exploded perspective view of an example of the filtration recovery device in accordance with aspects of the present disclosure.
Figure 14:
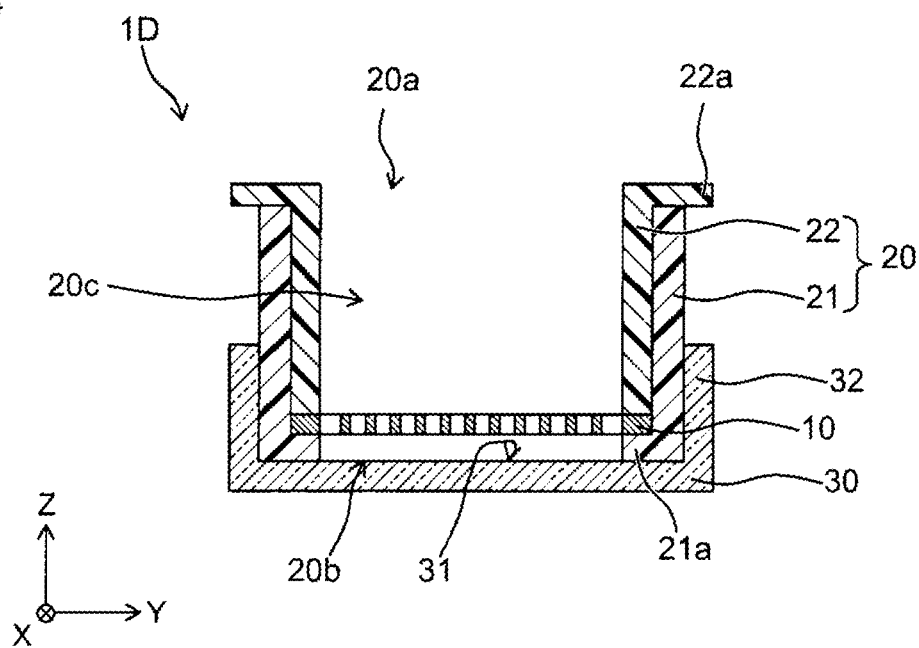
FIG. 14 is a schematic cross-sectional view of an example of the filtration recovery device in accordance with aspects of the present disclosure.

FIG. 12 is a schematic perspective view of an example of a filtration recovery device 1D according to an aspect of the present disclosure. FIG. 13 is a schematic exploded perspective view of the example of the filtration recovery device 1D according to an aspect of the present disclosure. FIG. 14 is a schematic cross-sectional view of the example of the filtration recovery device 1D according to an aspect of the present disclosure.

As illustrated in FIGS. 12 to 14, the filtration recovery device 1D includes a petri dish 30 attachably/detachably attached to the holder 20. The petri dish 30 is detached from the holder 20 when filtration is performed, and is attached to the holder 20 when recovery is performed. The petri dish 30 is formed in such a size that the one end of the holder 20 at which the discharge port 20b is provided can be accommodated.

The petri dish 30 has a bottom surface portion 31 and a side wall portion 32 that is formed along an outer edge of the bottom surface portion 31 and extends upward from the bottom surface portion 31. The petri dish 30 is attachably/detachably attached to the one end of the holder 20 at which the discharge port 20b is provided.

In a state where the petri dish 30 is attached to the one end of the holder 20 at which the discharge port 20b is provided, the bottom surface portion 31 is disposed at the one end of the holder 20 at which the discharge port 20b is provided. The side wall portion 32 is disposed so as to surround the outer wall of the holder 20.

As a result, the discharge port 20b is closed by the contact between the bottom surface portion 31 and the one end of the holder 20. Furthermore, by reducing or eliminating a space between the side wall portion 32 and the outer wall of the holder 20, a space to which the liquid 52 held inside the holder 20 leaks from the discharge port 20b is reduced or eliminated.

According to an aspect of the present disclosure, the bottom surface portion 31 of the petri dish 30 is formed in a flat shape. The side wall portion 32 of the petri dish 30 is disposed along the outer wall of the holder 20, and makes surface contact with the outer wall of the holder 20.

Furthermore, an inner side wall of the side wall portion 32 of the petri dish 30 makes surface contact with the outer wall of the holder 20. Specifically, the inner side wall of the side wall portion 32 of the petri dish 30 makes surface contact with the outer wall of the first holder 21. As a result, the contact area between the petri dish 30 and the holder 20 can be increased, and the sealing performance of the filtration recovery device 1D can be improved. That is, it is possible to suppress leakage of the liquid 52 held inside the holder 20 to the outside of the holder 20.

According to the filtration recovery device 1D according to an aspect of the present disclosure, the following effects can be obtained.

In the filtration recovery device 1D, the petri dish 30 having the bottom surface portion 31 and the side wall portion 32 that is formed along the outer edge of the bottom surface portion 31 and extends upward from the bottom surface portion 31 is attachably/detachably attached to the one end of the holder 20 at which the discharge port 20b is provided. This configuration makes it possible to further suppress the leakage of the liquid 52 from the discharge port 20b when the filtration object 51 is recovered. Accordingly, it is possible to more easily recover the filtration object 51.

Furthermore, since the leakage of the liquid 52 can be further suppressed, the adjustment of the liquid amount of the liquid 52 held inside the holder 20 becomes easier. This makes it possible to more easily perform a concentration adjustment and the like of a cell suspension.

Note that in an aspect of the present disclosure, the example in which the side wall portion 32 of the petri dish 30 makes surface contact with the outer wall of the holder 20 has been described, but the configuration is not limited thereto. The side wall portion 32 of the petri dish 30 need not make surface contact with the outer wall of the holder 20. It is sufficient that the leakage of the liquid 52 from the discharge port 20b can be suppressed by reducing the space between the side wall portion 32 of the petri dish 30 and the outer wall of the holder 20.

Figure 15:
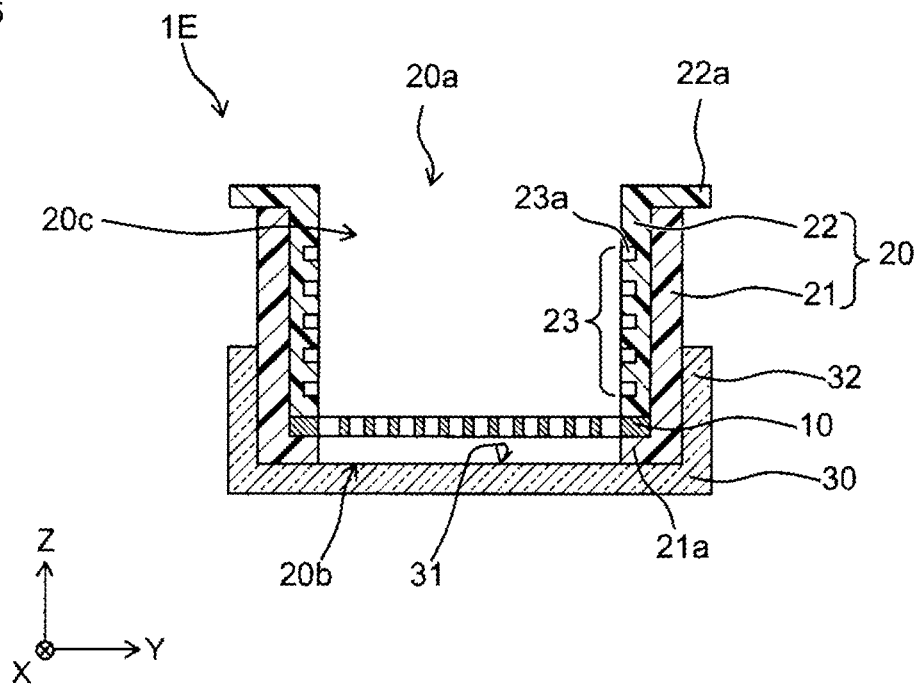
FIG. 15 is a schematic configuration diagram of a filtration recovery device of a modification in accordance with aspects of the present disclosure.

FIG. 15 is a schematic configuration diagram of a filtration recovery device 1E of a modification according to an aspect of the present disclosure. As illustrated in FIG. 15, in the filtration recovery device 1E, the liquid amount indication portion 23 may be provided in or on the inner wall of the holder 20. With this configuration, the user can easily check the liquid amount of the liquid 52 held inside the holder 20. This makes it possible to easily adjust the liquid amount of the liquid 52 may be required for the recovery.

A filtration recovery method according to an aspect of the present disclosure will be described.

According to an aspect of the present disclosure, points different from those in described above will be mainly described. According to an aspect of the present disclosure, the same or equivalent configurations as those described above will be described with the same reference numerals. In addition, according to an aspect of the present disclosure, descriptions overlapping with those described above will be omitted.

Aspects described below are different from aspects described above in a point that the filtration filter is detached from the filtration recovery device, and the filtration object is recovered by immersing the filtration filter in the liquid for recovery.

Figure 16:
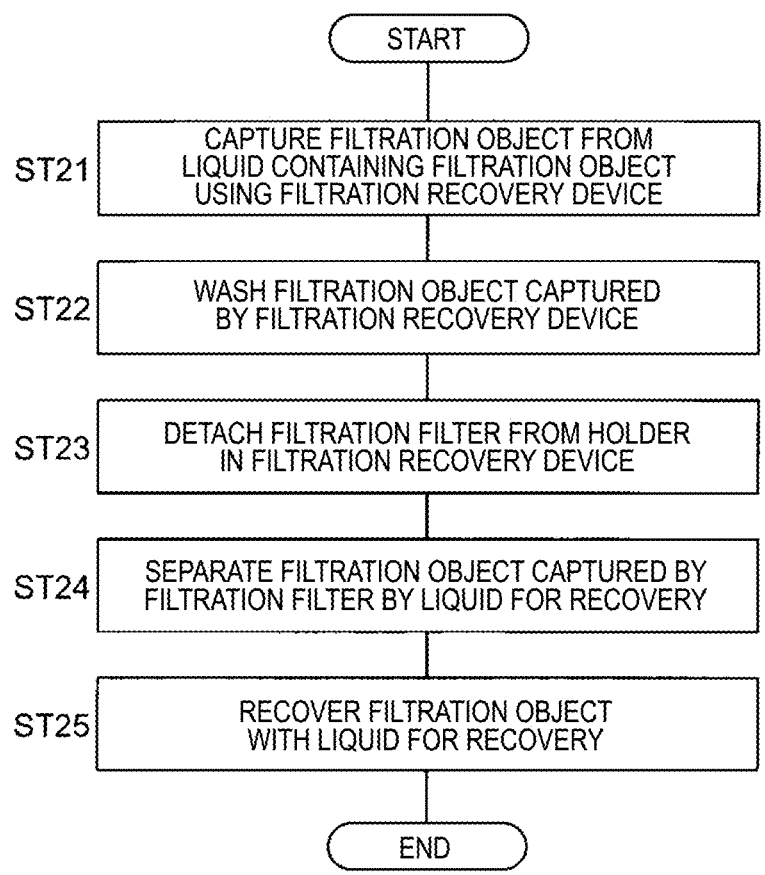
FIG. 16 is a flowchart of an example of a filtration recovery method in accordance with aspects of the present disclosure.

FIG. 16 is a flowchart of an example of a filtration recovery method according to an aspect of the present disclosure. As illustrated in FIG. 16, in step ST21, by filtering the liquid 50 containing the filtration object 51 by using the filtration recovery device 1A, the filtration object 51 is captured by the filtration filter 10. Specifically, the filtration recovery device 1A is attached to the centrifuge tube 40 (see FIG. 7), and the liquid 50 containing the filtration object 51 is introduced from the introduction port 20a of the holder 20 of the filtration recovery device 1A into the flow path 20c inside the holder 20.

The liquid 50 containing the filtration object 51 passes through the filtration filter 10 disposed in the flow path 20c, and is discharged from the discharge port 20b. As a result, the filtration object 51 larger than the through-hole 13 is captured by the filtration filter 10.

In step ST22, the filtration object 51 captured by the filtration recovery device 1A is washed. Specifically, a washing liquid is introduced to the filtration filter 10, and the filtration object 51 is washed.

In step ST23, in the filtration recovery device 1A, the filtration filter 10 is detached from the holder 20. Specifically, after the filtration recovery device 1A is detached from the centrifuge tube 40, the second holder 22 is detached from the first holder 21. Then, the filtration filter 10 is detached from the first holder 21. Furthermore, in step ST23, the filtration filter 10 is detached from the holder 20 in a state where the filtration object 51 is being captured on the first main surface PS1 of the filtration filter 10.

In step ST24, the filtration object 51 captured by the filtration filter 10 is separated by the liquid for recovery. Specifically, the filtration filter 10 is immersed in the liquid for recovery stored in a container. As a result, the filtration object is released from the first main surface PS1 of the filtration filter 10. Alternatively, the filtration object becomes easy to be released from the filtration filter 10.

In step ST25, the filtration object 51 is recovered together with the liquid in which the filtration filter 10 is immersed. For example, by using a pipette, the filtration object 51 is recovered with the liquid.

As described above, in the filtration recovery method according to an aspect of the present disclosure, by executing steps ST21 to ST25, the filtration object 51 can be recovered together with the liquid for recovery.

According to the filtration recovery method according to an aspect of the present disclosure, the following effects can be obtained.

In the filtration recovery method according to an aspect of the present disclosure, after filtering out the filtration object 51 by the filtration recovery device 1A, the filtration filter 10 is detached from the holder 20, and the filtration filter 10 is immersed in the liquid for recovery. As a result, the filtration object 51 captured by the filtration filter 10 is released from the filtration filter 10, and it is therefore possible to easily recover the filtration object 51.

Note that according to an aspect of the present disclosure, the example in which, in step ST24, the filtration filter 10 is immersed in the liquid for recovery has been described, but the configuration is not limited thereto. For example, in step ST24, the liquid for recovery may be poured onto the filtration filter 10. In this case, in step ST25, the filtration object 51 released from the filtration filter 10 by pouring the liquid for recovery onto the filtration filter 10 is recovered together with the liquid for recovery.

In the filtration recovery method according to an aspect of the present disclosure, step ST22 may not be an essential step.

A filtration recovery method according to an aspect of the present disclosure will be described.

According to an aspect of the present disclosure, points different from those in described above will be mainly described. According to an aspect of the present disclosure, the same or equivalent configurations as those described above will be described with the same reference numerals. In addition, according to an aspect of the present disclosure, descriptions overlapping with those described above will be omitted.

Aspects described below are different from aspects described above in a point that a cell is separated from a cell aggregate.

Figure 17:
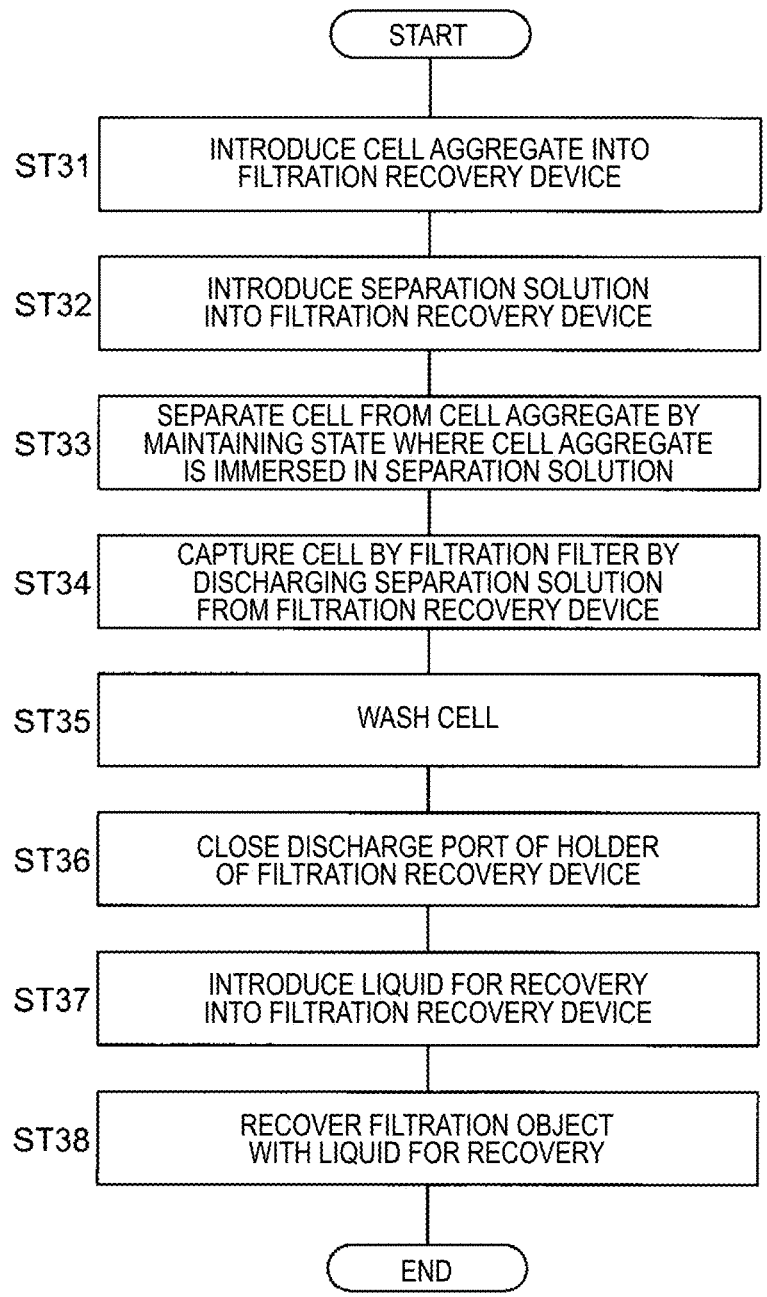
FIG. 17 is a flowchart of an example of a filtration recovery method in accordance with aspects of the present disclosure.

FIG. 17 is a flowchart of an example of a filtration recovery method according to an aspect of the present disclosure. As illustrated in FIG. 17, in step ST31, a cell aggregate is introduced into the filtration recovery device 1A. Specifically, the cell aggregate is disposed on the first main surface PS1 of the filtration filter 10 in the holder 20.

In step ST32, a separation solution is introduced into the filtration recovery device 1A. Specifically, the separation solution is introduced from the introduction port 20a of the holder 20 in a state where the discharge port 20b of the holder 20 is closed, and the cell aggregate disposed on the filtration filter 10 is immersed in the separation solution.

According to an aspect of the present disclosure, a trypsin solution was used as the separation solution.

In step ST33, a cell is separated from the cell aggregate by maintaining the state where the cell aggregate is immersed in the separation solution. Specifically, the state where the cell aggregate is immersed in the separation solution is maintained for a prescribed time. The prescribed time is, for example, five minutes.

In step ST34, by discharging the separation solution from the filtration recovery device 1A, the cell is captured by the filtration filter 10. Specifically, the discharge port 20b of the holder 20 of the filtration recovery device 1A is opened, and the separation solution is discharged from the discharge port 20b. With this, the cell is captured by the filtration filter 10.

In step ST35 the cell captured by the filtration recovery device 1A is washed. Specifically, a washing liquid is introduced to the filtration filter 10, and the cell is washed.

In step ST36, the discharge port 20b of the holder 20 of the filtration recovery device 1A is closed. Specifically, the one end of the holder 20 at which the discharge port 20b is provided is disposed on a flat surface, and the one end of the holder 20 and the flat surface are brought into surface contact with each other.

In step ST37, the liquid for recovery is introduced into the filtration recovery device 1A. Specifically, the liquid for recovery is introduced from the introduction port 20a of the holder 20, and the liquid for recovery is held in the flow path 20c of the holder 20.

In step ST38, the cell is recovered together with the liquid for recovery. For example, by using the pipette 53, the cell is recovered with the liquid for recovery held in the flow path 20c of the holder 20.

As described above, in the filtration recovery method according to an aspect of the present disclosure, by executing steps ST31 to ST38, the cell separated from the cell aggregate can be recovered together with the liquid for recovery.

According to the filtration recovery method according to an aspect of the present disclosure, the following effects can be obtained.

In the filtration recovery method according to an aspect of the present disclosure, the cell can be separated from the cell aggregate, and the separated cell can be easily recovered together with the liquid for recovery.

As described above, the filtration recovery method according to an aspect of the present disclosure can be used as a method for separating a cell from a cell aggregate. In the method as described above, it is possible to reduce the time during which the cell is in contact with the separation solution (for example, trypsin solution), and it is therefore possible to reduce influence on the cell. Furthermore, in comparison with centrifugation or the like, reaggregation of the separated cell is unlikely to occur, and physical damage to the cell can also be reduced.

Note that in aspects of the present disclosure, the example in which, in the step ST32, the separation solution is introduced from the introduction port 20a of the holder 20 has been described, but the configuration is not limited thereto. In step ST32, the filtration recovery device 1A may be immersed in a container in which the separation solution is held.

In the filtration recovery method according to an aspect of the present disclosure, step ST35 may not be an essential configuration.

A filtration recovery method according to an aspect of the present disclosure will be described.

According to an aspect of the present disclosure, points different from those in described above will be mainly described. According to an aspect of the present disclosure, the same or equivalent configurations as those described above will be described with the same reference numerals. In addition, according to an aspect of the present disclosure, descriptions overlapping with those described above will be omitted.

Aspects described below are different from aspects described above in a point that a solvent is introduced into the filtration recovery device before introducing the liquid containing the filtration object into the filtration recovery device.

Figure 18:
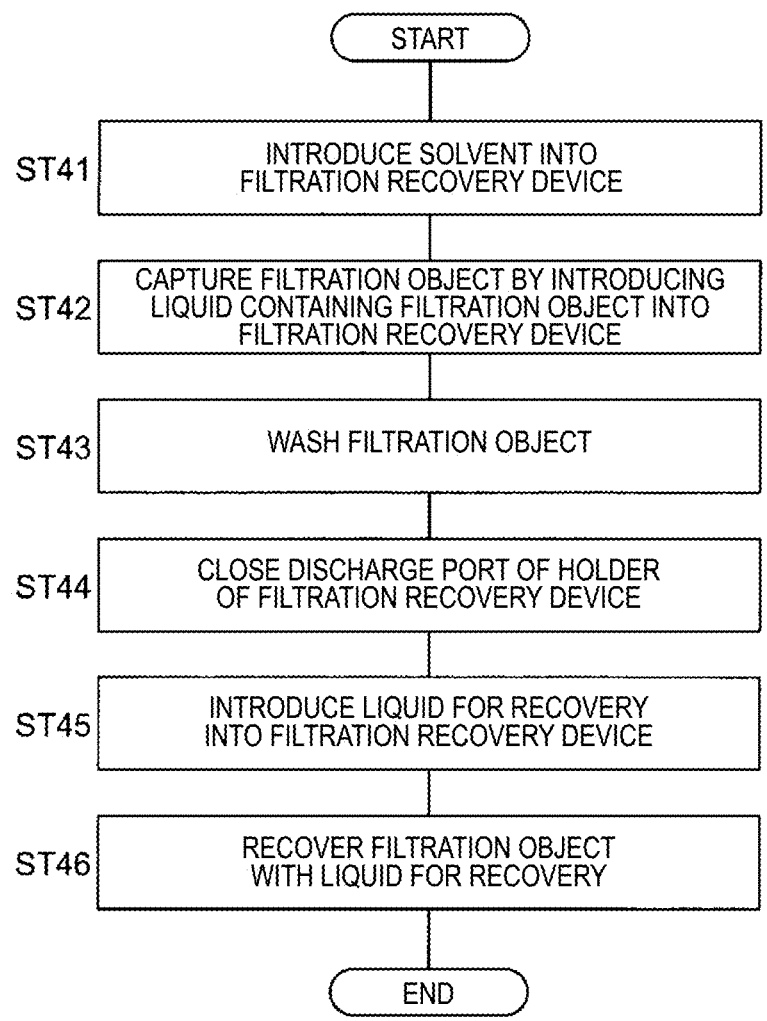
FIG. 18 is a flowchart of an example of a filtration recovery method in accordance with aspects of the present disclosure.

FIG. 18 is a flowchart of an example of a filtration recovery method according to an aspect of the present disclosure. As illustrated in FIG. 18, in step ST41, a solvent is introduced into the filtration recovery device 1A. Specifically, the solvent is introduced from the introduction port 20a of the holder 20 in a state where the discharge port 20b of the holder 20 is closed. According to an aspect of the present disclosure, the solvent is the same as the liquid 50 containing the filtration object 51.

In step ST42, by introducing the liquid 50 containing the filtration object 51 into the filtration recovery device 1A, the filtration object 51 is captured by the filtration filter 10. Specifically, the discharge port 20b of the holder 20 is opened, and the liquid 50 containing the filtration object 51 is introduced from the introduction port 20a of the holder 20.

The liquid 50 containing the filtration object 51 passes through the filtration filter 10 disposed in the flow path 20c, and is discharged from the discharge port 20b. As a result, the filtration object 51 larger than the through-hole 13 is captured on the first main surface PS1 of the filtration filter 10.

In step ST43, the filtration object 51 captured by the filtration recovery device 1A is washed. Specifically, a washing liquid is introduced to the filtration filter 10, and the filtration object 51 is washed. In step ST44, the discharge port 20b of the holder 20 of the filtration recovery device 1A is closed. In step ST45, the liquid for recovery is introduced into the filtration recovery device 1A. Specifically, the liquid for recovery is introduced from the introduction port 20a of the holder 20. Since the discharge port 20b of the holder 20 is in a closed state through step ST44, the liquid 52 is held in the flow path 20c inside the holder 20. As a result, the filtration object 51 is released from the filtration filter 10 and floats in the liquid for recovery held inside the holder 20. In step ST46, the filtration object 51 is recovered together with the liquid for recovery held in the filtration recovery device 1A. As described above, in the filtration recovery method according to an aspect of the present disclosure, by executing steps ST41 to ST46, the filtration object 51 can be recovered together with the liquid for recovery.

According to the filtration recovery method according to an aspect of the present disclosure, the following effects can be obtained.

In the filtration recovery method according to an aspect of the present disclosure, before the liquid 50 containing the filtration object 51 is introduced into the filtration recovery device 1A, the solvent is introduced into the filtration recovery device 1A.

Note that in aspects of the present disclosure, the example in which, in the step ST41, the solvent is introduced from the introduction port 20a of the holder 20 in the state where the discharge port 20b of the holder 20 is closed has been described, but the configuration is not limited thereto. For example, in step ST41, by immersing the filtration recovery device 1A in a container holding the solvent, the solvent may be introduced into the filtration recovery device 1A.

In the filtration recovery method according to an aspect of the present disclosure, step ST43 may not be an essential configuration.

According to an aspect of the present disclosure, filtration and recovery of a cell suspension were performed using the filtration recovery device 1A according to an aspect of the present disclosure, and the recovered cell suspension was evaluated. Furthermore, evaluation was performed using Comparative Examples 1 to 3 under the same conditions as described above.

Information of the filtration recovery device 1A used in Example 1 is shown in Table 1. Note that the configuration of the filtration recovery device 1A of Example 1 has been described above, and the description thereof will therefore be omitted. In addition, the interval of the through-holes shown in Table 1 means the dimension of the width of the filter base body portion 14 that divides two adjacent through-holes 13.

TABLE 1

| | |
|---|---|
| Outer Diameter of Filtration Filter 10 | 25 mm |
| Thickness of Filtration Filter 10 | 1.8 μm |
| Diameter of Filter Portion 11 | 20 mm |
| Width of Frame Portion 12 | 2.5 mm |
| Shape of Through-Hole 13 | Square |
| Arrangement of Through-Holes 13 | Square Lattice Arrangement |
| Size d of Through-Hole 13 | One Side 4.5 μm |
| Interval b of Through-Holes 13 | 2.0 μm |
| Opening Ratio | 48% |
| Outer Diameter of Holder 20 | 27 mm |
| Inner Diameter of Holder 20 | 25 mm |
| Height of Holder 20 | 25 mm |
| Height of Projection Portion 21a | 4.1 mm |
| Volume in Holder 20 between Filtration Filter 10 and Discharge Port 20b | 2.0 mL |

Note that the "Outer Diameter of Holder 20" corresponds to the outer diameter of the first holder 21. The "Inner Diameter of Holder 20" corresponds to the inner diameter of the second holder 22. The "Height of Holder 20" corresponds to the length of the holder 20 in the Z direction. The "Height of Projection Portion 21a" means the length of the projection portion 21a in the Z direction.

Figure 19:
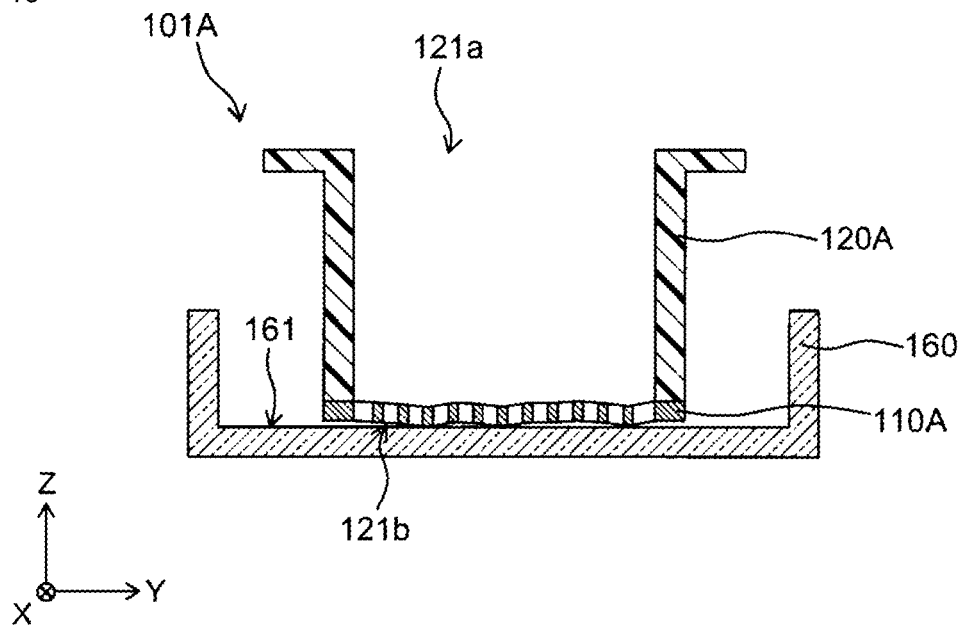
FIG. 19 is a schematic configuration diagram of a filtration recovery device of Comparative Example 1, in accordance with aspects of the present disclosure.

Comparative Example 1 will be described. FIG. 19 is a schematic configuration diagram of a filtration recovery device 101A of Comparative Example 1. As illustrated in FIG. 19, in the filtration recovery device 101A of Comparative Example 1, a filtration filter 110A is disposed at a discharge port 121b of a holder 120A. In Comparative Example 1, in the case where the filtration recovery device 101A is disposed on a bottom surface portion 161 of a petri dish 160, a state occurs in which the discharge port 121b cannot be closed due to undulation of the filtration filter 110A.

Figure 20:
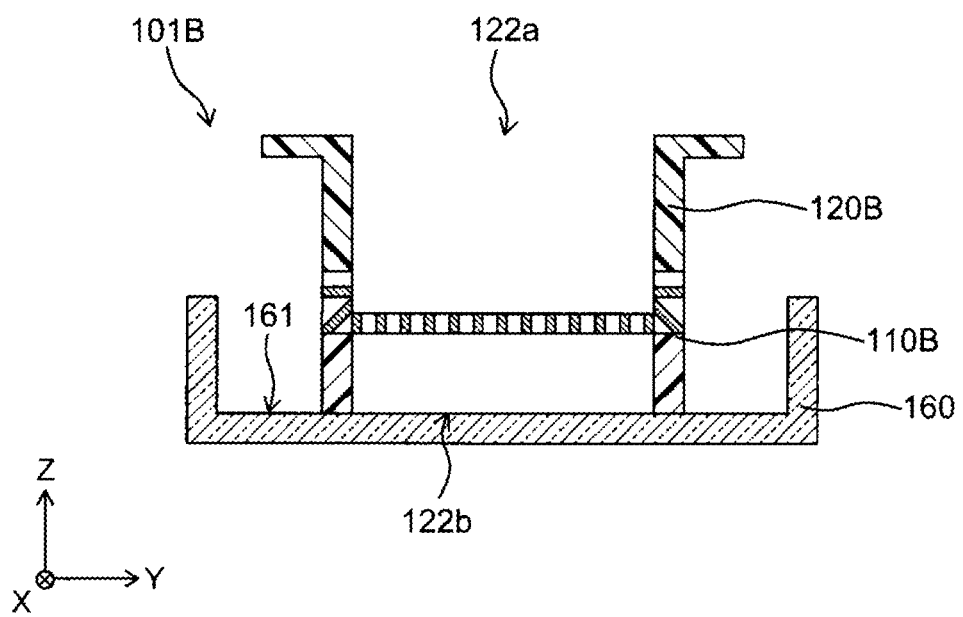
FIG. 20 is a schematic configuration diagram of a filtration recovery device of Comparative Example 2, in accordance with aspects of the present disclosure.

Comparative Example 2 will be described. FIG. 20 is a schematic configuration diagram of a filtration recovery device 101B of Comparative Example 2. As illustrated in FIG. 20, in the filtration recovery device 101B of Comparative Example 2, a filtration filter 110B is disposed above a discharge port 122b of a holder 120B. The filtration filter 110B forms part of a side wall of the holder 120B. In Comparative Example 2, in the case where the liquid 52 for recovery is introduced from an introduction port 122a, the liquid 52 leaks from the portion of the filtration filter 110B that forms the part of the side wall of the holder 120B. Accordingly, the liquid cannot be held inside the holder 120B, and a certain amount of liquid cannot be recovered. Furthermore, the time during which a cell which is the filtration object comes into contact with the atmosphere and the filtration filter 110B becomes longer, and the cell is damaged. There is the possibility that this causes reduction in activity of the cell.

Figure 21:
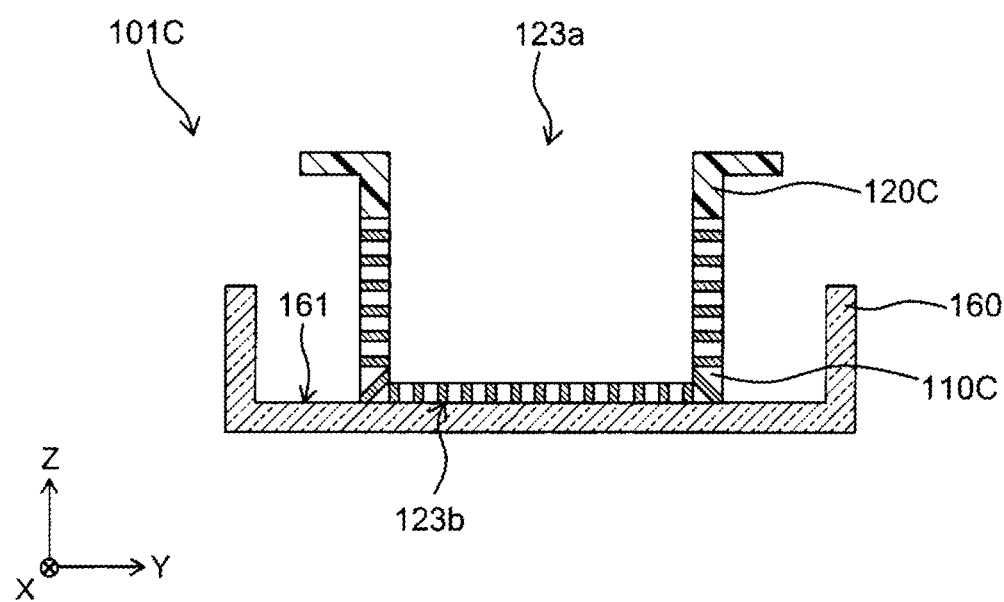
FIG. 21 is a schematic configuration diagram of a filtration recovery device of Comparative Example 3, in accordance with aspects of the present disclosure.

Comparative Example 3 will be described. FIG. 21 is a schematic configuration diagram of a filtration recovery device 101C of Comparative Example 3. As illustrated in FIG. 21, in the filtration recovery device 101C of Comparative Example 3, a resin filter is used as the filtration filter 110C. In the filtration recovery device 101C of Comparative Example 3, the filtration filter 110C is disposed at the discharge port 123b of a holder 120C. Furthermore, a filtration filter 110C forms part of a side wall of the holder 120C. In Comparative Example 3, in the case where the liquid 52 for recovery is introduced from an introduction port 123a, the liquid 52 leaks from the portion of the filtration filter 110C that forms the part of the side wall of the holder 120C.

Note that in Comparative Examples 1 and 2, the filtration filters 110A and 110B are designed with the same dimensions as those of the filtration filter 10 of Example 1. In Comparative Example 3, the resin filter is used as the filtration filter 110C, but a resin filter with dimensions corresponding to those of the filtration filter 10 of Example 1 in terms of the outer diameter, the thickness, and the dimension of the through-hole of the filter is used. In addition, in Comparative Examples 1 to 3, the holders 120A, 120B, and 120C are designed with the same dimensions as those of the holder 20 of Example 1 except for the dimension of the height of the projection portion. Note that in each of Comparative Examples 1 and 3, the projection portion is not included, and in Comparative Example 2, the height of the projection portion is 4.1 mm.

In Example 1 and Comparative Examples 1 to 3, the filtration recovery devices 1A, 101A, 101B, and 101C were each attached to an upper portion of a 50 mL centrifuge tube, and cell suspensions were respectively introduced from the introduction ports 20a, 121a, 122a, and 123a, and filtration of each of the cell suspensions was performed. Table 2 shows conditions of the filtration performed in Example 1 and Comparative Examples 1 to 3.

TABLE 2

| Cell | HL-60 |
|---|---|
| Cell Size | 10 to 13 μm |
| Introduced Cell Concentration | $5.0 \times 10^5$ pieces/mL |
| Total Number of Cells | $2.5 \times 10^6$ pieces |
| Introduced Liquid Amount | 5 mL |

In Example 1, after 20 seconds from starting filtration using the filtration recovery device 1A, the cell suspension on the first main surface PS1 of the filtration filter 10 disappeared, and white turbidity on the first main surface PS1 by the captured cell was visually confirmed. A state where the cell suspension on the first main surface PS1 of the filtration filter 10 disappeared and the cell was captured on the first main surface PS1 was visually confirmed. Immediately after the confirmation, 5 mL of PBS (Phosphate Buffered Saline) was introduced from the introduction port 20a of the holder 20, and the cell captured on the filtration filter 10 was washed. In the same manner, in Comparative Examples 1 to 3 as well, filtration was performed using each of the filtration filters 110A, 110B, and 110C, and states where cells were respectively captured by the filtration filters 110A, 110B, and 110C were visually confirmed. Note that in Comparative Example 3, since the resin filter was used as the filtration filter 110C, the filtration was performed with suction at a pressure of 30 kPa. In Comparative Examples 1 to 3 as well, the cells respectively captured by the filtration filters 110A, 110B, and 110C were washed by the PBS.

After washing, in Example 1, the filtration recovery device 1A was disposed on the bottom surface portion 61 of the petri dish 60 having an outer diameter of 35 mm, and 5 mL of PBS was introduced from the introduction port 20a of the holder 20 as the liquid 52 for recovery. Next, the target recovery liquid amount of the cell suspension was set to 3 mL, and the cell suspension held inside the holder 20 was manually recovered by the pipette 53. In the same manner, in Comparative Examples 1 to 3 as well, the filtration recovery devices 101A, 101B, and 101C were each disposed on the bottom surface portion 161 of the petri dish 160, and 5 mL of PBS was introduced into each of the holders 120A, 120B, and 120C. Next, the target recovery liquid amount of the cell suspension was set to 3 mL, and the cell suspension held inside each of the holders 120A, 120B, and 120C was manually recovered by the pipette 53.

For the cell suspensions recovered in Example 1 and Comparative Examples 1 to 3, a recovered liquid amount, the number of cells in the recovered cell suspension, a cell recovery rate, and a cell survival rate were evaluated.

The recovery liquid amount was measured using a graduated cylinder. In addition, the total number of cells, the number of living cells, and the number of dead cells, in 1 mL, of cells stained with trypan blue were measured using an automated cell counter (CountessIIFL manufactured by Invitrogen).

The cell suspension recovery rate, the number of cells, the cell recovery rate, and the cell survival rate may be calculated using the following calculation equation.

(Cell Suspension Recovery Rate [%])=(Recovered Liquid Amount [mL])/(Target Recovery Liquid Amount [mL])×100

(The Number of Cells [pieces])=(Measured Value of Automated Cell Counter [pieces/mL])×(Recovery Liquid Amount [mL])

(Cell Recovery Rate [%])=(The Number of Cells in Suspension After Filtration [pieces])/(The Number of Cells in Suspension Before Filtration [pieces])×100

(Cell Survival Rate [%])=(The Number of Living Cells [pieces])/(The Total Number of Cells [pieces])×100

The evaluation results are shown in Table 3.

TABLE 3

| | Example 1 | Comparative Example 1 | Comparative Example 2 | Comparative Example 3 |
|---|---|---|---|---|
| Liquid Amount of Recovered Cell Suspension | 2.97 mL | 1.56 mL | 0.30 mL | 0.28 mL |
| The Number of Cells in Recovered Cell Suspension | $2.4 \times 10^6$ pieces | $1.3 \times 10^6$ pieces | $0.75 \times 10^6$ pieces | $0.78 \times 10^6$ pieces |
| Cell Suspension Recovery Rate to Target Recovery | 99% | 52% | 10% | 9% |

TABLE 3-continued

|  | Example 1 | Comparative Example 1 | Comparative Example 2 | Comparative Example 3 |
|---|---|---|---|---|
| Liquid Amount (3 ml) |  |  |  |  |
| Cell Recovery Rate | 96% | 52% | 30% | 31% |
| Cell Survival Rate | 98% | 96% | 90% | 89% |

As shown in Table 3, in Example 1, the cell recovery rate was 96%, and the cell survival rate was 98%. In addition, in comparison with the target recovery liquid amount 3 mL, the liquid amount of the cell suspension recovered by using the pipette 53 was 2.97 mL. That is, the cell suspension recovery rate to the target recovery liquid amount was 99%.

As described above, in Example 1, the cell recovery rate is 96%, which is extremely high, and thus it is understood that the cells captured by the filtration filter 10 can be easily recovered. In addition, in Example 1, since the cell survival rate is 98%, it is understood that the cells can be recovered without damaging the cells. Furthermore, in Example 1, since the liquid amount of the recovered cell suspension is 99% of the target recovery liquid amount, it is understood that a desired liquid amount of cell suspension can be recovered.

In Comparative Example 1, the cell recovery rate was 52%, and the cell survival rate was 96%. However, the liquid amount of the recovered cell suspension was 1.56 mL, and the cell suspension recovery rate to the target recovery liquid amount was 52%.

In Comparative Example 1, the liquid amount of the recovered cell suspension is smaller than Example 1. In Comparative Example 1, since the filtration filter 110A is disposed at the discharge port 121b of the holder 120A and the filtration filter 110A itself has undulation, it is thought that the discharge port 121b is not closed by the bottom surface portion 161 of the petri dish 160, and the cell suspension has leaked from the discharge port 121b.

In Comparative Example 2, the cell recovery rate was 30%, and the cell survival rate was 90%. Additionally, in Comparative Example 2, the liquid amount of the recovered cell suspension was 0.30 mL, and the cell suspension recovery rate to the target recovery liquid amount was 10%.

In Comparative Example 2, the cell recovery rate is lower and the liquid amount of the recovered cell suspension is also smaller than Example 1. In Comparative Example 2, part of the side wall of the holder 120B is formed by the filtration filter 110B. Accordingly, the cell suspension held inside the holder 120B leaks from the portion of the filtration filter 110B which forms the part of the side surface of the holder 120B. As a result, it is thought that the liquid amount of the recovered cell suspension decreases. Furthermore, since it is difficult to hold the liquid inside the holder 120B, it is thought that the cells are difficult to be released from the filtration filter 110B, and the cell recovery rate also drops.

In Comparative Example 3, the cell recovery rate was 31%, and the cell survival rate was 89%. Additionally, in Comparative Example 3, the liquid amount of the recovered cell suspension was 0.28 mL, and the cell suspension recovery rate to the target recovery liquid amount was 9%.

In Comparative Example 3, the cell recovery rate and the cell survival rate are lower and the liquid amount of the recovered cell suspension is also smaller than Example 1. In Comparative Example 3, the filtration filter 110B is disposed at the discharge port 122b of the holder 120C. Furthermore, the filtration filter 110C forms part of the side wall of the holder 120C. Accordingly, in Comparative Example 3, the cell suspension in the holder 120C leaks from the portion of the filtration filter 110C which forms the part of the side wall of the holder 120C. Accordingly, as a result, it is thought that the liquid amount of the recovered cell suspension decreases. Furthermore, since it is difficult to hold the liquid inside the holder 120C, it is thought that the cells are difficult to be released from the filtration filter 110C, and the cell recovery rate also drops.

Furthermore, in Comparative Example 3, the resin filter is used as the filtration filter 110C. Accordingly, since the liquid does not pass through the filtration filter 110C unless external stress such as suction or the like is applied, the inside of the centrifuge tube is brought into a negative pressure state. As a result, since the cell enters the inside of the through-hole of the filtration filter 110C and cannot be recovered, pipetting may be required. Furthermore, as a result of observing the recovered cells under a microscope, it was confirmed that the cells were deformed and damaged. It is thought that, due to the influence of filtration and pipetting in the negative pressure state, the deformation or damage of the cells occur, and the cell survival rate drops.

Another exemplary aspect will be described. Filtration and recovery of a cell suspension were performed using the filtration recovery device 1A according to an aspect of the present disclosure, and the recovered cell suspension was evaluated. Note that in Example 2, since the experiment was performed with a smaller liquid amount than in Example 1, a device having a smaller dimension than that of the filtration recovery device 1A of Example 1 was used.

Information of the filtration recovery device 1A used in Example 2 is shown in Table 4. Note that the configuration of the filtration recovery device 1A of Example 2 has been described above, and the description thereof will therefore be omitted. In addition, the interval of the through-holes 13 shown in Table 4 means the dimension of the width of the filter base body portion 14 that divides two adjacent through-holes 13.

TABLE 4

| | |
|---|---|
| Outer Diameter of Filtration Filter 10 | 12 mm |
| Thickness of Filtration Filter 10 | 1.8 μm |
| Diameter of Filter Portion 11 | 10 mm |
| Width of Frame Portion 12 | 1.0 mm |
| Shape of Through-Hole 13 | Square |
| Arrangement of Through-Holes 13 | Square Lattice Arrangement |
| Size d of Through-Hole 13 | One Side 4.5 μm |
| Interval b of Through-Holes 13 | 2.0 μm |
| Opening Ratio | 48% |
| Outer Diameter of Holder 20 | 14 mm |
| Inner Diameter of Holder 20 | 12 mm |
| Height of Holder 20 | 15 mm |
| Height of Projection Portion 21a | 1.8 mm |
| Volume in Holder 20 between Filtration Filter 10 and Discharge Port 20b | 0.2 mL |

In Example 2, the filtration recovery device 1A was attached to an upper portion of a 15 ml centrifuge tube, and a cell suspension was introduced from the introduction port 20a, and filtration of the cell suspension was performed. Table 5 shows conditions of the filtration performed in Example 2.

TABLE 5

| | |
|---|---|
| Cell | HL-60 |
| Cell Size | 10 to 13 μm |

TABLE 5-continued

| Introduced Cell Concentration | $1.0 \times 10^5$ pieces/mL |
| --- | --- |
| Total Number of Cells | $1.0 \times 10^6$ pieces |
| Introduced Liquid Amount | 10 mL |

In Example 2, after 60 seconds from starting filtration using the filtration recovery device 1A, the cell suspension on the first main surface PS1 of the filtration filter 10 disappeared, and a state where the cell was captured on the first main surface PS1 was visually confirmed. Immediately after the confirmation, 5 mL of PBS (Phosphate Buffered Saline) was introduced from the introduction port 20a of the holder 20, and the cell captured on the filtration filter 10 was washed.

After washing, the filtration recovery device 1A was disposed on the bottom surface portion 61 of the petri dish 60 having an outer diameter of 35 mm, and 5 mL of PBS was introduced from the introduction port 20a of the holder 20 as the liquid 52 for recovery. Next, the target recovery liquid amount of the cell suspension was set to 0.5 mL, and the cell suspension held inside the holder 20 was manually recovered by the pipette 53.

For the cell suspension recovered in Example 2, a recovered liquid amount, the number of cells in the recovered cell suspension, a cell recovery rate, and a cell survival rate were evaluated. The evaluation results are shown in Table 6.

TABLE 6

| | Example 2 |
| --- | --- |
| Liquid Amount of Recovered Cell Suspension | 0.48 mL |
| The Number of Cells in Recovered Cell Suspension | $9.8 \times 10^5$ pieces |
| Cell Suspension Recovery Rate to Target Recovery Liquid Amount (0.5 ml) | 96% |
| Cell Recovery Rate | 98% |
| Cell Survival Rate | 98% |

As shown in Table 6, in Example 2, the cell recovery rate was 98%, and the cell survival rate was 98%. In addition, in comparison with the target recovery liquid amount 0.5 mL, the liquid amount of the cell suspension manually recovered by using the pipette 53 was 0.48 mL. That is, the cell suspension recovery rate to the target recovery liquid amount was 96%.

As described above, in the filtration recovery device 1A, it is also possible to easily recover a small amount of cell suspension such as 0.5 mL.

Although the present invention has been fully described in connection with the preferred embodiments with reference to the accompanying drawings, various changes and modifications are apparent to those skilled in the art. It is to be understood that such changes and modifications are included within the scope of the present invention as defined by the appended claims unless they depart therefrom.

The filtration recovery device according to the present invention is useful for application of recovering biologically derived substances in fluid at a high recovery rate, and is effectively applied to a regenerative medical industry, a food industry, and the like.

REFERENCE SIGNS LIST 1A, 1B, 1C, 1D, 1E FILTRATION RECOVERY DEVICE
10, 10A FILTRATION FILTER
11 FILTER PORTION
12 FRAME PORTION
13 THROUGH-HOLE
14 FILTER BASE BODY PORTION
20 HOLDER
20a INTRODUCTION PORT
20b DISCHARGE PORT
20c FLOW PATH
21 FIRST HOLDER
21a, 21b PROJECTION PORTION
21aa FIRST MAIN BODY PORTION
21ab UPPER SURFACE
22 SECOND HOLDER
22a FLANGE
22b HANDLE
22aa SECOND MAIN BODY PORTION
23 LIQUID AMOUNT INDICATION PORTION
23a GROOVE
24 HOLE
30 PETRI DISH
31 BOTTOM SURFACE PORTION
32 SIDE WALL PORTION
40 CENTRIFUGE TUBE
50 LIQUID
51 FILTRATION OBJECT
52 LIQUID FOR RECOVERY
53 PIPETTE
60 PETRI DISH
61 BOTTOM SURFACE PORTION
101A, 101B, 101C FILTRATION RECOVERY DEVICE
110A, 110B, 110C FILTRATION FILTER
120A, 120B, 120C HOLDER
121a, 122a, 123a INTRODUCTION PORT
121b, 122b, 123b DISCHARGE PORT
160 PETRI DISH
161 BOTTOM SURFACE PORTION

What is claimed is:
1. A filtration recovery device comprising:
a holder including an introduction port configured to introduce a liquid, a discharge port configured to discharge the liquid, and a flow path configured to communicate the introduction port and the discharge port with each other;
a filtration filter including a plurality of through-holes disposed in the flow path between the introduction port and the discharge port of the holder; and
a projection portion that projects toward an inner side portion of the holder and is formed on an inner wall of the holder,
wherein the projection portion is configured to hold the filtration filter;
wherein the holder further includes a first holder having a tubular shape and includes the projection portion;
wherein a second holder having a tubular shape is configured to be fitted into the first holder,
wherein the filtration filter is configured to be held between the projection portion and an end of the second holder;
wherein the first holder further includes a first main body portion having a tubular shape and having a first end portion located on a side of the introduction port of the holder and a second end portion located on a side of the discharge port of the holder,
wherein the second holder includes a second main body portion having a tubular shape and having a third end portion located on the side of the introduction port of the holder and a fourth end portion located on the side of the discharge port of the holder, wherein the filtration filter includes a filter portion having the plurality of through-holes, and frame that surround an outer periphery of the filter portion,
wherein the projection portion is provided at the second end portion of the first main body portion of the first holder,
wherein an inner wall of the first main body portion is in surface contact with an outer wall of the second main body portion, and
wherein the frame of the filtration filter is held between the fourth end portion of the second main body portion and an upper surface of the projection portion.

2. The filtration recovery device according to claim 1, wherein the projection portion is located at a first end of the holder, wherein the first end of the holder includes the discharge port, and
wherein the filtration filter is located closer to the discharge port than the introduction port.

3. The filtration recovery device according to claim 2 wherein the first end of the holder is configured to make contact with a flat surface.

4. The filtration recovery device according to claim 2, further comprising:
a petri dish having a bottom surface portion and a side wall portion formed along an outer edge of the bottom surface portion and extending upward from the bottom surface portion, and configured to be attachable and detachable from the first end of the holder that includes the discharge port,
wherein the bottom surface portion of the petri dish is disposed at the first end of the holder that includes the discharge port, and
the side wall portion of the petri dish surrounds an outer wall of the holder.

5. The filtration recovery device according to claim 4, wherein an inner side wall of the side wall portion of the petri dish is configured to be in surface contact with the outer wall of the holder.

6. The filtration recovery device according to claim 1, wherein the second holder has a flange extending from the outer wall of the second main body portion toward an outer side portion of the second holder at the third end portion of the second main body portion, and
the flange is in contact with the first end portion of the first main body portion.

7. The filtration recovery device according to claim 1, wherein the frame of the filtration filter is held, in a thickness direction, between the projection portion of the first holder and the end of the second holder, in a state of continuously extending in a direction from the filter portion toward the frame.

8. The filtration recovery device according to claim 1, further comprising a liquid amount indication portion in or on the inner wall of the holder and configured to indicate a liquid amount of a liquid held inside the holder when the discharge port is closed.

9. The filtration recovery device according to claim 1, wherein the filtration filter contains at least one of a metal or a metal oxide as a main component.

10. A filtration recovery method for filtering a liquid containing a filtration object and recovering the filtration object, the filtration recovery method comprising:
capturing the filtration object, by using a filtration recovery device that includes a filtration filter having a plurality of through-holes, and a holder having an introduction port configured to introduce a liquid,
wherein the holder further includes a first holder having a tubular shape and includes a projection portion that holds the filtration filter;
wherein the projection portion projects toward an inner side portion of the holder and is formed on an inner wall of the holder,
wherein a second holder having a tubular shape is configured to be fitted into the first holder,
holding, by using the projection portion and an end of the second holder, the filtration filter between the projection portion and the end of the second holder,
wherein the first holder further includes a first main body portion having a tubular shape and having a first end portion located on a side of the introduction port of the holder and a second end portion located on a side of a discharge port of the holder,
wherein the second holder includes a second main body portion having a tubular shape and having a third end portion located on the side of the introduction port of the holder and a fourth end portion located on the side of the discharge port of the holder, and that surrounds an outer periphery of the filtration filter by a frame,
wherein the projection portion is provided at the second end portion of the first main body portion, and
wherein an inner wall of the first main body portion contacts an outer wall of the second main body portion;
holding, by using the fourth end portion of the second main body portion and an upper surface of the projection portion, the frame of the filtration filter between the fourth end portion of the second main body portion and the upper surface of the projection portion,
the discharge port configured to discharge the liquid, and a flow path configured to communicate the introduction port and the discharge port with each other, and in which the filtration filter is disposed in the flow path between the introduction port and the discharge port of the holder, by filtering the liquid containing the filtration object, the filtration object located on the filtration filter;
closing the discharge port of the holder of the filtration recovery device;
introducing a liquid for recovery from the introduction port of the holder of the filtration recovery device; and
recovering the filtration object with the liquid for recovery held in the holder of the filtration recovery device.

11. The filtration recovery method according to claim 10, wherein closing the discharge port of the holder of the filtration recovery device includes disposing an end of the holder at which the discharge port is located on a bottom surface portion of a petri dish.

12. The filtration recovery method according to claim 10, further comprising indicating, by a liquid amount indication portion located in or on an inner wall of the holder, an amount of liquid held inside the holder when the discharge port is closed; and
wherein introducing the liquid for recovery includes introducing the liquid for recovery based on the liquid amount indication portion.

13. A filtration recovery method for filtering a liquid containing a filtration object and recovering the filtration object, the filtration recovery method comprising
capturing, by using a filtration recovery device that includes a filtration filter having a plurality of through-holes, and a holder having an introduction port configured to introduce the liquid, wherein the holder further includes a first holder having a tubular shape and
includes a projection portion that holds the filtration
filter;
wherein the projection portion projects toward an inner
side portion of the holder and is formed on an inner
wall of the holder,
wherein a second holder having a tubular shape is
configured to be fitted into the first holder,
holding, by using the projection portion and an end of the
second holder, the filtration filter between the projection portion and the end of the second holder,
wherein the first holder further includes a first main
body portion having a tubular shape and having a
first end portion located on a side of the introduction
port of the holder and a second end portion located
on a side of a discharge port of the holder,
wherein the second holder includes a second main body
portion having a tubular shape and having a third end
portion located on the side of the introduction port of
the holder and a fourth end portion located on the
side of the discharge port of the holder, and that
surrounds an outer periphery of the filtration filter by
a frame,
wherein the projection portion is provided at the second
end portion of the first main body portion, and
wherein an inner wall of the first main body portion
contacts an outer wall of the second main body
portion;
holding, by using the fourth end portion of the second
main body portion and an upper surface of the projection portion, the frame of the filtration filter between the
fourth end portion of the second main body portion and
the upper surface of the projection portion,
the discharge port configured to discharge the liquid,
and a flow path configured to communicate the
introduction port and the discharge port with each
other, and in which the filtration filter is disposed in
the flow path between the introduction port and the
discharge port of the holder, by filtering the liquid
containing the filtration object, the filtration object
located on the filtration filter;
detaching the filtration filter from the holder of the
filtration recovery device;
separating the filtration object captured by the filtration
filter by a liquid for recovery; and
recovering the filtration object with the liquid for recovery.

14. The filtration recovery method according to claim 13,
wherein separating the filtration object captured includes
immersing the filtration filter in the liquid for recovery.

15. A filtration recovery method for separating a cell from
a cell aggregate and filtering out and recovering the cell, the
filtration recovery method comprising steps of:
introducing the cell aggregate into a filtration recovery
device that includes a filtration filter having a plurality
of through-holes, and a holder having an introduction
port configured to introduce a liquid, wherein the
holder further includes a first holder having a tubular
shape and includes a projection portion that holds the
filtration filter;
wherein the projection portion projects toward an inner
side portion of the holder and is formed on an inner
wall of the holder,
wherein a second holder having a tubular shape is
configured to be fitted into the first holder,
holding, by using the projection portion and an end of the
second holder, the filtration filter between the projection portion and the end of the second holder,
wherein the first holder further includes a first main
body portion having a tubular shape and having a
first end portion located on a side of the introduction
port of the holder and a second end portion located
on a side of a discharge port of the holder,
wherein the second holder includes a second main body
portion having a tubular shape and having a third end
portion located on the side of the introduction port of
the holder and a fourth end portion located on the
side of the discharge port of the holder, and that
surrounds an outer periphery of the filtration filter by
a frame,
wherein the projection portion is provided at the second
end portion of the first main body portion, and
wherein an inner wall of the first main body portion
contacts an outer wall of the second main body
portion;
holding, by using the fourth end portion of the second
main body portion and an upper surface of the projection portion, the frame of the filtration filter between the
fourth end portion of the second main body portion and
the upper surface of the projection portion,
the discharge port configured to discharge the liquid,
and a flow path configured to communicate the
introduction port and the discharge port with each
other, and in which the filtration filter is disposed in
the flow path between the introduction port and the
discharge port of the holder;
introducing a separation solution into the filtration recovery device;
separating a cell from the cell aggregate by maintaining a
state where the cell aggregate is immersed in the
separation solution;
capturing the cell by the filtration filter by discharging the
separation solution from the filtration recovery device;
closing the discharge port of the holder of the filtration
recovery device;
introducing a liquid for recovery from the introduction
port of the holder of the filtration recovery device; and
recovering the cell with the liquid for recovery held in the
holder of the filtration recovery device.

16. A filtration recovery method for filtering a liquid
containing a filtration object and recovering the filtration
object, the filtration recovery method comprising steps of:
introducing a solvent into a filtration recovery device that
includes a filtration filter having a plurality of through-
holes, and a holder having an introduction port configured to introduce the liquid, wherein the holder further
includes a first holder having a tubular shape and
includes a projection portion that holds the filtration
filter;
wherein the projection portion projects toward an inner
side portion of the holder and is formed on an inner
wall of the holder,
wherein a second holder having a tubular shape is
configured to be fitted into the first holder,
holding, by using the projection portion and an end of the
second holder, the filtration filter between the projection portion and the end of the second holder,
wherein the first holder further includes a first main
body portion having a tubular shape and having a
first end portion located on a side of the introduction
port of the holder and a second end portion located
on a side of a discharge port of the holder, wherein the second holder includes a second main body portion having a tubular shape and having a third end portion located on the side of the introduction port of the holder and a fourth end portion located on the side of the discharge port of the holder, and that surrounds an outer periphery of the filtration filter by a frame, wherein the projection portion is provided at the second end portion of the first main body portion, and wherein an inner wall of the first main body portion contacts an outer wall of the second main body portion;

holding, by using the fourth end portion of the second main body portion and an upper surface of the projection portion, the frame of the filtration filter between the fourth end portion of the second main body portion and the upper surface of the projection portion, the discharge port configured to discharge the liquid, and a flow path configured to communicate the introduction port and the discharge port with each other, and in which the filtration filter is disposed in the flow path between the introduction port and the discharge port of the holder;

capturing, by introducing the liquid containing the filtration object into the filtration recovery device, the filtration object by the filtration filter;

closing the discharge port of the holder of the filtration recovery device;

introducing a liquid for recovery from the introduction port of the holder of the filtration recovery device; and recovering the filtration object with the liquid for recovery held in the holder of the filtration recovery device.

17. The filtration recovery method according to claim 16, further comprising washing the filtration object with a washing liquid after capturing.

* * * * *